United States Patent
Kondo et al.

(10) Patent No.: US 10,047,091 B2
(45) Date of Patent: Aug. 14, 2018

(54) IONIC LIQUID, LUBRICATING AGENT, AND MAGNETIC RECORDING MEDIUM

(71) Applicant: Dexerials Corporation, Shinagawa-ku, Tokyo (JP)

(72) Inventors: Hirofumi Kondo, Tokyo (JP); Kouki Hatsuda, Tokyo (JP); Nobuo Tano, Tokyo (JP); Makiya Ito, Tokyo (JP); Kyungsung Yun, Tokyo (JP); Masayoshi Watanabe, Kanagawa (JP)

(73) Assignee: Dexerials Corporation, Tokyo (JP)

( * ) Notice: Subject to any disclaimer, the term of this patent is extended or adjusted under 35 U.S.C. 154(b) by 415 days.

(21) Appl. No.: 14/655,457

(22) PCT Filed: Dec. 27, 2013

(86) PCT No.: PCT/JP2013/085213
§ 371 (c)(1),
(2) Date: Jun. 25, 2015

(87) PCT Pub. No.: WO2014/104342
PCT Pub. Date: Jul. 3, 2014

(65) Prior Publication Data
US 2015/0353558 A1    Dec. 10, 2015

(30) Foreign Application Priority Data

| Dec. 28, 2012 | (JP) | 2012-288528 |
| Mar. 1, 2013 | (JP) | 2013-040759 |
| Aug. 26, 2013 | (JP) | 2013-174811 |
| Dec. 26, 2013 | (JP) | 2013-270198 |

(51) Int. Cl.
*C07D 487/04* (2006.01)
*C07C 311/48* (2006.01)
(Continued)

(52) U.S. Cl.
CPC .......... *C07D 487/04* (2013.01); *C07C 211/03* (2013.01); *C07C 211/07* (2013.01);
(Continued)

(58) Field of Classification Search
CPC ... C07D 285/15; C07D 487/04; C07C 311/48; C07C 211/07; C07C 211/21;
(Continued)

(56) References Cited

U.S. PATENT DOCUMENTS

2004/0023831 A1    2/2004  Kono et al.
2011/0177428 A1    7/2011  Dai et al.

FOREIGN PATENT DOCUMENTS

CN    101490091    7/2009
JP    64-049118    2/1989
(Continued)

OTHER PUBLICATIONS https://pubchem.ncbi.nlm.nih.gov/compound/octadecylamine, Aug. 2017, pp. 1-42.*
(Continued)

*Primary Examiner* — Holly Rickman
(74) *Attorney, Agent, or Firm* — Carmody Torrance Sandak & Hennessey LLP

(57) ABSTRACT

A lubricating agent including an ionic liquid formed from a Bronsted acid (HX) and a Bronsted base (B), wherein the Bronsted base has a linear hydrocarbon group having 10 or more carbon atoms and the difference between the pKa value of the Bronsted acid in water and the pKa value of the Bronsted base in water is 12 or more.

11 Claims, 8 Drawing Sheets

(51) Int. Cl.
| | |
|---|---|
| *C07C 211/07* | (2006.01) |
| *C07C 309/06* | (2006.01) |
| *C07C 309/04* | (2006.01) |
| *C07C 211/21* | (2006.01) |
| *C07C 211/03* | (2006.01) |
| *C07D 285/15* | (2006.01) |
| *C10M 159/12* | (2006.01) |
| *C10M 105/58* | (2006.01) |
| *C10M 105/72* | (2006.01) |
| *G11B 5/725* | (2006.01) |
| *C10M 171/00* | (2006.01) |
| *C10M 105/60* | (2006.01) |
| *C10M 105/70* | (2006.01) |

(52) U.S. Cl.
CPC .......... *C07C 211/21* (2013.01); *C07C 309/04* (2013.01); *C07C 309/06* (2013.01); *C07C 311/48* (2013.01); *C07D 285/15* (2013.01); *C10M 105/58* (2013.01); *C10M 105/60* (2013.01); *C10M 105/70* (2013.01); *C10M 105/72* (2013.01); *C10M 159/12* (2013.01); *C10M 171/00* (2013.01); *G11B 5/725* (2013.01); *C10M 2215/003* (2013.01); *C10M 2215/041* (2013.01); *C10M 2215/2203* (2013.01); *C10M 2219/0406* (2013.01); *C10N 2220/027* (2013.01); *C10N 2230/06* (2013.01); *C10N 2230/74* (2013.01); *C10N 2240/204* (2013.01)

(58) Field of Classification Search
CPC ... C07C 211/03; C07C 309/06; C07C 309/04; C10N 2220/04; C10M 105/72; G11B 5/725
See application file for complete search history.

(56) References Cited

FOREIGN PATENT DOCUMENTS

| | | |
|---|---|---|
| JP | 01-207263 | 8/1989 |
| JP | 2581090 | 11/1996 |
| JP | 2629725 | 4/1997 |

OTHER PUBLICATIONS http://www.emergingcontaminants.eu/index.php/background-info/Factsheets-PFOS-intro/Factsheets-PFOS-properties, Aug. 2017.*

English machine translation of JP H01-207263, Aug. 1989, pp. 1-5.* http://evans.rc.fas.harvard.edu/pdf/evans_pKa_table.pdf, Aug. 2017.*

English Machine translation of CN 101490091, Jul. 2009, pp. 1-20.*

Kohler, F. et al., Molecular Interactions in Mixtures of Carboxylic Acids with Amines. 1. Melting Curves and Viscosities, J. Phys. Chem., vol. 85, No. 17, Aug. 1981, pp. 2520-2524.

Kohler, F., et al., Molecular Interactions in Mixtures of Carboxylic Acids with Amines. 2. Volumetric, Conductimetric, and NMR Properties, J. Phys. Chem., vol. 85, No. 17, Aug. 1981, pp. 2524-2529.

Kondo, H., et al., Novel Lubricants for Magnetic Thin Film Media, Journal of Magnetics Society of Japan, vol. 13, Supplement No. S1, 1989, pp. 213-218.

Kondo, F., et al., Frictional Properties of Novel Lubricants for Magnetic Thin Film Media, IEEE Transactions on Magnetics, vol. 26, No. 5, Sep. 1990, pp. 2691-2693.

Kondo, F., et al., Comparison of an Amide and Amine Salt as Friction Modifiers for a Magnetic Thin Film Medium, Tribology Transactions, vol. 37, No. 1, Jan. 1994, pp. 99-104.

Yoshizawa, M., Ionic Liquids by Proton Transfer: Vapor Pressure, Conductivity, and the Relevance of $\Delta pK_a$ from Aqueous Solutions, J. Am. Chem. Soc., vol. 125, 2003, pp. 15411-15419.

Stoimenovski, J., et al., Ionicity and Proton Transfer in Protic Ionic Liquids, Phys. Chem. Chem. Phys., vol. 12, 2010, pp. 10341-10347.

Luo, H., Ultrastable Superbase-Derived Protic Ionic Liquids, J. Phys. Chem. B, vol. 113, No. 13, 2009, pp. 4181-4183.

Miran, M.S., Physicochemical Properties Determined by $\Delta pK_a$ for Protic Ionic Liquids Based on an Organic Super-Strong Base with Various Brønsted acids, Phys. Chem. Chem. Phys., vol. 14, 2012, pp. 5178-5186.

Kondo, H., et al., New Ionic Liquid Lubricants for Magnetic Thin Film Media, AbstractBook of 12$^{th}$ Joint MMM/Intermag Conference, 2012.

Kondo, H., et al., New Ionic Liquid Lubricants for Magnetic Thin Film Media, 12$^{th}$ Joint MMM/Intermag Conference, 2012.

Kondo, H., et al., Novel Ionic Lubricants for Magnetic Thin Film Media, 2013, pp. 1-5.

Extended European Search Report issued for corresponding EP application dated May 23, 2016.

Singapore Examination Report dated Jul. 21, 2016 issued for corresponding Singapore application.

Chinese Office Action dated Oct. 26, 2016 issue for corresponding Chinese application.

State Intellectual Property Office of the People's Republic of China, Chinese Office Action for corresponding Chinese Application No. 201380068521.4, dated Oct. 26, 2017.

* cited by examiner

IONIC LIQUID, LUBRICATING AGENT, AND MAGNETIC RECORDING MEDIUM

TECHNICAL FIELD

The present invention relates to an ionic liquid comprised of a Bronsted acid and a Bronsted base, a lubricating agent containing the ionic liquid, and a magnetic recording medium using the lubricating agent.

BACKGROUND ART

Conventionally, in a thin film magnetic recording medium, a lubricating agent is applied onto a surface of a magnetic layer in order to reduce friction and wear between a magnetic head and a surface of the medium. An actual film thickness of the lubricating agent is at the molecular level in order to avoid adhesion such as stiction. Therefore, it's no exaggeration to say that the most important thing in the thin film magnetic recording medium is to select a lubricating agent having excellent wear resistance under every environment.

It is important to allow the lubricating agent remain on the surface of the medium without detachment, spin-off, or chemical deterioration throughout a service life of the magnetic recording medium. The more difficult it is to allow the lubricating agent remain on the surface of the medium, the smoother the surface of the thin film magnetic recording medium is. This is because the thin film magnetic recording medium has no ability for replenishing the lubricating agent, unlike a coating type magnetic recording medium.

In the case where the lubricating agent is only weakly adhered to a protecting film on the surface of the magnetic layer, a large quantity of lubricating agent is required because the film thickness of the lubricating agent is decreased upon heating or sliding to thereby accelerate wear. The large quantity of lubricating agent results in a migrating lubricating agent which can have the ability for replenishing the lubricating agent removed through wear. However, there is a dilemma that an excess of lubricating agent causes the film thickness of the lubricating agent to be greater than surface roughness to thereby cause a problem related to adhesion, and eventually the stiction contributing to drive failure, which is fatal. The problem related to friction has not been satisfyingly solved by conventional perfluoropolyether (PFPE) based lubricating agents.

Particularly, in a thin film magnetic recording medium having high surface smoothness, a novel lubricating agent has been molecularly designed and synthesized in order to solve the trade-off. Many reports on a lubricating property of PFPE have been submitted. Thus, the lubricating agent is very important for the magnetic recording medium.

Table 1 shows chemical structures of representative PFPE based lubricating agents.

TABLE 1

| Fomblin based lubricating agents | |
|---|---|
| | X—$CF_2(OCF_2CF_2)_n(OCF_2)_mOCF_2$—X (0.5 < n/m < 1) |
| Z | X = —$OCF_3$ |
| Z-DOL | X = —$CH_2OH$ |
| Z-DIAC | X = —COOH |
| Z-Tetraol | X = —$CH_2$ $OCH_2CHCH_2OH$<br>         OH |
| AM2001 | X = —$CH_2OCH_2$— 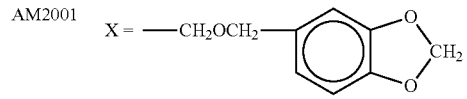 |

| Other lubricating agents | |
|---|---|
| A20H | $HOCH_2CF_2(OCF_2CF_2)_n(OCF_2)_mOCF_2CH_2O$—[structure] |
| Mono | F—$(CF_2CF_2C_2O)_1$—$CF_2CF_2CH_2$—$N(C_3H_7)_2$ |

Z-DOL in Table 1 is one of commonly used lubricating agents for thin film magnetic recording media. Z-tetraol (ZTMD) is those in which a functional hydroxyl group is additionally introduced in a main chain of PFPE, which has been reported to enhance reliability of the drive while reducing gap of a head-media interface. A20H has been reported to prevent the main chain of PFPE from being decomposed by a Lewis acid or a Lewis base, and improve tribological characteristics. Meanwhile, Mono has a different polymeric main chain and polar group from the above described PFPE, that is, polynormal propyloxy and amine, respectively; and has been reported to decrease adhesive interactions in near contact.

However, a common solid lubricating agent which is believed to have a high melting point and thermal stability interferes with highly sensitive electromagnetic conversion process and deteriorates wear characteristics due to wear debris produced in a running track when the agent is scraped by the head. The liquid lubricating agent as described above has a migrating property which is an ability in which a lubricating agent removed through wear is replenished with a lubricating agent migrated from the adjacent lubricating layer. However, due to the migrating property, the lubricating agent is decreased by spin-off from the surface of the disk during disk operation especially under a high temperature, so that a protective function is lost. Therefore, a lubricating agent having high viscosity and low volatility has been suitably used, which allows for low evaporation rate and long service life of the disk drive.

In view of these lubricating mechanisms, a low friction and low wear lubricating agent used in the thin film magnetic recording medium is required to have the following requirements:
(1) low volatility;
(2) low surface tension for surface replenishing ability;
(3) interaction between a terminal polar group and a surface of a disk;
(4) high thermal and oxidative stability to prevent decomposition or a decrease during use;
(5) chemically inert to metal, glass, and polymer, and no wear debris produced by a head or a guide;
(6) no toxicity or flammability;
(7) excellent boundary lubricating property; and
(8) solubility in organic solvents.

Recently, an ionic liquid has been attracting attention as one of environmental friendly solvents for synthesizing organic or inorganic materials in electricity storage materials, separation technologies, and catalyst technologies. The ionic liquid is broadly categorized into a molten salt having a low melting point, and generally refers to the molten salt having the melting point of 100° C. or lower. Important properties of the ionic liquid used as the lubricating agent include low volatility, no flammability, thermal stability, and excellent solubility. Therefore, the ionic liquid is expected to be applied as a novel lubricating agent under an extreme environment such as in vacuum or in a high temperature due to its characteristic. It has also been known that use of the ionic liquid in a gate of a single self-assembled quantum dot transistor improves the controllability of the transistor by a factor of one hundred over a conventional one. In this technique, the ionic liquid forms an electric double layer and serves as an about 1 nm-thick insulating film to thereby obtain a large electric capacity.

For example, use of a certain ionic liquid may reduce friction and wear on a metal or ceramic surface in comparison to a conventional hydrocarbon based lubricating agent. For example, it has been reported that, in the case where an imidazole cation based ionic liquid is synthesized by replacing with a fluoroalkyl group, and alkylimidazolium tetrafluoroborate or hexafluorophosphate is used on steel, aluminium, copper, single crystal $SiO_2$, silicon, or sialon ceramics (Si—Al—O—N), it shows more excellent tribological characteristics than cyclic phosphazene (X-1P) or PFPE. It has also been reported that an ammonium based ionic liquid reduces friction in from elastohydrodynamic to boundary lubrication region compared with a base oil. In addition, an ionic liquid has examined for an effect as an additive for the base oil, or researched on a chemical and tribological chemical reaction in order to understand its lubricating mechanism. However, there are few application examples as the magnetic recording medium.

Among ionic liquids, a protic ionic liquid is a generic designation of compounds formed through a chemical reaction between a Bronsted acid and a Bronsted base in equal amounts. Research by Kohler et al. related to an interaction between carboxylic acid and amine has been reported a 1:1 complex of carboxylic acid and amine in chemically equal amounts can be formed (e.g., see NPLs 1 and 2). Perfluorooctanoic acid alkyl ammonium salt is the protic ionic liquid (PIL), and has been reported to have an effect of reducing friction in the magnetic recording medium significantly higher than the above described Z-DOL (see, PTLs 1 and 2, and NPLs 3 to 5).

However, these perfluorocarboxylic acid ammonium salts have a weak interaction between a cation and an anion in the reaction shown by the following Reaction scheme (A). Therefore, the equilibrium is shifted towards left side under a high temperature in accordance with Le Chatelier's law to thereby produce dissociated neutral compounds, leading to thermal instability. That is, proton transfer occurs under the high temperature and the equilibrium is shifted towards the neutral substance to thereby dissociate (e.g., see NPL 6).

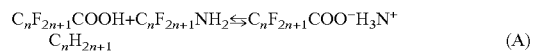
$$C_nH_{2n+1} \tag{A}$$

The limit of a surface recording density of a hard disk is said to be 1 Tb/in² to 2.5 Tb/in². At present, the limit is being approached, but energetic development has been continued for increasing a capacity on the assumption of refining magnetic particles. The technologies for increasing the capacity include decreasing effective flying height or introducing Shingle Write (BMP).

Additionally, "Heat Assisted Magnetic Recording" is known as a next-generation recording technology. FIG. 3 is a schematic view illustrating the heat assisted magnetic recording. In the technology, a recording portion is heated with laser upon recording/reproduction, and therefore, there is a problem that durability is deteriorated due to evaporation or decomposition of the lubricating agent on a surface of the magnetic layer. In the heat assisted magnetic recording, the magnetic recording medium may be exposed to a high temperature which is said to be 400° C. or higher even in a short time. Therefore, commonly used lubricating agents for the thin film magnetic recording media, Z-DOL and a carboxylic acid ammonium salt based lubricating agent, are concerned about their thermal stability.

The ionic liquid is generally a substance having high thermal stability because it forms ions as described above. The equilibrium thereof is shown in the following Scheme 1.

Scheme 1: Scheme of acid-base reaction $HA + H_2O \rightleftarrows H_3O^+ + A^-$ $B + H_2O \rightleftarrows HB^+ + OH^-$ $A^- + HB \rightarrow A^-HB^+$ $HA + B + 2H_2O \rightleftarrows A^-HB^+ + H_3O^+ + OH^-$ In the above Scheme, HA denotes a Bronsted acid, and B denotes a Bronsted base. The acid (HA) and the base (B) react with each other as shown in Scheme 1 to thereby form a salt ($A^-HB^+$).

Herein, the dissociation constants $K_{a1}$ and $K_{b2}$ of the acid and the base can be shown by the following Scheme 2 using concentrations thereof.

Scheme 2: Relationship between acid and base dissociation constants

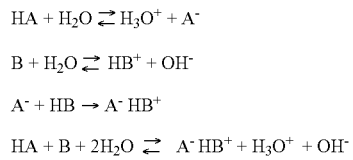

The $K_{a1}$ and the $K_{b2}$ vary widely depending on substances, and, in some cases, they have the large number of digits. However, the large number of digits is inconvenient for handling, so that it is often expressed as the negative common logarithm. That is, as shown in the following Scheme 3, it is defined that $-\log_{10} K_{a1}$ is equal to $pK_{a1}$. Obviously, the smaller $pK_{a1}$ is, the stronger the acidity is.

Next, the difference between the dissociation constants of the acid and the base, $\Delta pKa$, will be discussed. A reaction between an acid and a base is influenced by their acidity or basicity (or acidity of a conjugate acid), and the difference of acidity $\Delta pKa$ can be shown by the following Scheme 3.

Scheme 3: Relationship between acidic and basic pKas $$pK_{a1} = -\log \frac{[A^-][H_3O^+]}{[HA]}$$

$$pK_{b2} = -\log \frac{[HB^+][OH^-]}{[B]}$$

$$pK_{a2} = 14 - pK_{b2} = 14 + \log \frac{[BH^+][OH^-]}{[B]}$$

$$\Delta pK_a = pK_{a2} - pK_{a1} = -pK_{a1} - pK_{b2} + 14 = \log \frac{[A^-][BH^+][H_3O^+][OH^-]}{[HA][B]}$$

$$= \log \frac{[A^-][HB^+]}{[HA][B]} = \log \frac{[A^-HB^+]}{[HA][B]}$$

As can be seen from the above Scheme, the $\Delta pKa$ becomes larger as the salt concentration $[A^-HB^+]$ becomes larger relative to the acid and base concentrations.

In particular, Yoshizawa et al. have been reported that, when the difference between the pKa value of the acid and the pKa value of the base ($\Delta pKa$) is 10 or more, the proton transfer is more likely to occur, and

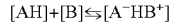

the equilibrium is shifted towards an ion side (right side) to thereby enhance stability (e.g., see NPL 6). However, MacFarlane et al. have been reported that the proton transfer occur and an ionized PIL can be obtained as long as the $\Delta pKa$ is at least 4 (e.g., see NPL 7). Dai et al. have been described that, based on an energy level diagram, thermal stability of the protic ionic liquid can be greatly improved by combining a strong acid with a strong base (e.g., see NPL 8). Watanabe et al. have reported that proton transferability and thermal stability of the protic ionic liquid greatly depend on $\Delta pKa$, and, therefore, when DBU (1,8-diazabicyclo[5.4.0] undec-7-ene) is used as the base, the ionic liquid is greatly improved in the thermal stability by using an acid having a pKa value so as to give the $\Delta pKa$ of 15 or more (e.g., see NPL 9). However, it has not been sufficiently discussed what level of $\Delta pKa$ is required for a certain application.

CITATION LIST

Patent Literature

PTL 1: Japanese Patent (JP-B) No. 2581090
PTL 2: JP-B No. 2629725

Non-Patent Literature

NPL 1: Kohler, F., Atrops, H., Kalall, H., Liebermann, E., Wilhelm, E., Ratkovics, F., & Salamon, T., (1981a). Molecular Interactions in Mixtures of Carboxylic acids with amines. 1. Melting Curves and Viscosities, J. Phys. Chem. Vol. 85, No. 17, (August 1981), pp. 2520-2524, ISSN: 0022-3654
NPL 2: Kohler, F., Gopal, R., Goetze, G., Atrops, H., Demiriz, M. A., Liebermann, E., Wilhelm, E., Ratkovics, F., & Palagyl, B., (1981). Molecular Interactions in Mixtures of Carboxylic acids with amines. 2. Volumetric, Conductimetric, and NMR Properties, J. Phys. Chem. Vol. 85, No. 17, pp. 2524-2529, ISSN: 0022-3654
NPL 3: Kondo, H., Seto, J., Haga. S., Ozawa, K., (1989) Novel Lubricants for Magnetic Thin Film Media, Magnetic Soc. Japan, Vol. 13, Suppl. No. S1, pp. 213-218
NPL 4: Kondo, H., Seki, A., Watanabe, H., & Seto, J., (1990). Frictional Properties of Novel Lubricants for Magnetic Thin Film Media, IEEE Trans. Magn. Vol. 26, No. 5, (September 1990), pp. 2691-2693, ISSN: 0018-9464
NPL 5: Kondo, H., Seki, A., & Kita, A., (1994a). Comparison of an Amide and Amine Salt as Friction Modifiers for a Magnetic Thin Film Medium. Tribology Trans. Vol. 37, No. 1, (January 1994), pp. 99-105, ISSN: 0569-8197
NPL 6: Yoshizawa, M., Xu, W., Angell, C. A., Ionic Liquids by Proton Transfer: Vapor pressure, Conductivity, and the Relevance of $\Delta pKa$ from Aqueous Solutions, J. Am. Chem. Soc., Vol. 125, pp. 15411-15419 (2003)
NPL 7: Stoimenovski, J., Izgorodina, E. I., MacFalane, D. R., Ionicity and proton transfer in protic ionic liquids, Phys. Chem. Chem. Phys., 2010, Vol. 12, 10341 Luo, H., Baker, G. A., Lee, J. S., Pagni, R. M., Dai, S., Ultrastable Superbase-Derived Protic Ionic Liquids, J. Phys. Chem. B Vol. 113, pp. 4181-4183 (2009)
NPL 8: Luo, H., Baker, G. A., Lee, J. S., Pagni, R. M., Dai, S., Ultrastable Superbase-Derived Protic Ionic Liquids, J. Phys. Chem. B Vol. 113, pp. 4181-4183 (2009)
NPL 9: Miran, M. S., Kinoshita, H., Yasuda, T., Susan, M. A. B. H., Watanabe, M., Physicochemical Properties Determined by $\Delta pKa$ for Protic Ionic Liquids Based on an Organic Super-strong Base with Various Bronsted Acids, Phys. Chem. Chem. Phys., Vol 14, pp. 5178-5186 (2012)

SUMMARY OF INVENTION

Technical Problem

As described above, in the art of magnetic recording media, there still remains drawbacks with regard to practical characteristics such as runnability, wear resistance, and durability due to deficiency in performance of a lubricating agent.

The present invention has been made in view of the foregoing, and provides an ionic liquid having an excellent lubricating property even under a high temperature, a lubricating agent having an excellent lubricating property even under a high temperature, and a magnetic recording medium having an excellent practical characteristic.

Solution to Problem

The present inventors conducted extensive studies, and have found that the aforementioned objects can be achieved by defining, in an ionic liquid, the number of carbon atoms in a hydrocarbon group of a Bronsted base and a difference between a pKa value of a Bronsted acid and a pKa value of the Bronsted base. Thus, the present invention have been completed.

<1> A lubricating agent, including:
an ionic liquid formed from a Bronsted acid (HX) and a Bronsted base (B),
wherein the Bronsted base has a linear hydrocarbon group having 10 or more carbon atoms, and
wherein a difference between a pKa value of the Bronsted acid in water and a pKa value of the Bronsted base in water is 12 or more.

<2> The lubricating agent according to <1>, wherein the ionic liquid is represented by the following General Formula (1):

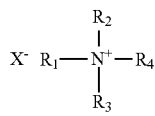

General Formula (1)

wherein at least one of $R_1$, $R_2$, $R_3$, and $R_4$ is a hydrogen atom, and at least one of $R_1$, $R_2$, $R_3$, and $R_4$ is a group which contains the linear hydrocarbon group having 10 or more carbon atoms.

<3> The lubricating agent according to <1>, wherein the Bronsted base is a cyclic amidine which contains the linear hydrocarbon group having 10 or more carbon atoms.

<4> The lubricating agent according to <3>, wherein the ionic liquid is represented by the following General Formula (2):

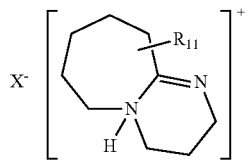

General Formula (2)

wherein $R_{11}$ denotes the linear hydrocarbon group having 10 or more carbon atoms and being attached to a carbon atom in a bicyclo ring.

<5> The lubricating agent according to any one of <1> to <4>, wherein the Bronsted acid is sulfonic acid.

<6> The lubricating agent according to any one of <1> to <5>, wherein the ionic liquid has an exothermic peak temperature determined by a differential thermal analysis (DTA) measurement of 370° C. or higher.

<7> The lubricating agent according to any one of <1> to <6>, wherein the hydrocarbon group is an alkyl group.

<8> A lubricating agent, including:
an ionic liquid formed from a Bronsted acid (HX) and a Bronsted base (B),
wherein the Bronsted base has a linear hydrocarbon group having 10 or more carbon atoms, and
wherein a difference between a pKa value of the Bronsted acid in acetonitrile and a pKa value of the Bronsted base in acetonitrile is 6 or more.

<9> The lubricating agent according to <8>, wherein the ionic liquid is represented by the following General Formula (1):

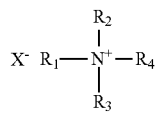

General Formula (1)

wherein at least one of $R_1$, $R_2$, $R_3$, and $R_4$ is a hydrogen atom, and at least one of $R_1$, $R_2$, $R_3$, and $R_4$ is a group which contains the linear hydrocarbon group having 10 or more carbon atoms.

<10> The lubricating agent according to <8>, wherein the Bronsted base is a cyclic amidine which contains the linear hydrocarbon group having 10 or more carbon atoms or a cyclic guanidine which contains the linear hydrocarbon group having 10 or more carbon atoms.

<11> The lubricating agent according to <10>, wherein the ionic liquid is represented by the following General Formula (2) or (3):

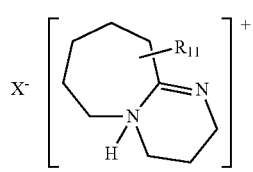

General Formula (2)

wherein $R_{11}$ denotes the linear hydrocarbon group having 10 or more carbon atoms and being attached to a carbon atom in a bicyclo ring,

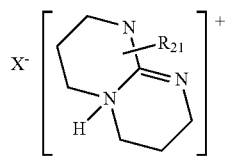

General Formula (3)

wherein $R_{21}$ denotes the linear hydrocarbon group having 10 or more carbon atoms and being attached to a carbon atom or a nitrogen atom in a bicyclo ring.

<12> The lubricating agent according to any one of <8> to <11>, wherein the ionic liquid has an exothermic peak temperature determined by a differential thermal analysis (DTA) measurement of 370° C. or higher.

<13> The lubricating agent according to any one of <8> to <12>, wherein the Bronsted acid is perfluoroalkyl sulfonic acid, a compound represented by the following Structural Formula (A), a compound represented by the following Structural Formula (B), a compound represented by the following Structural Formula (C), or a compound represented by the following Structural Formula (D):

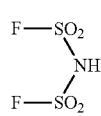

Structural Formula (A)

-continued

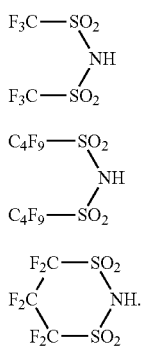
Structural Formula (B)

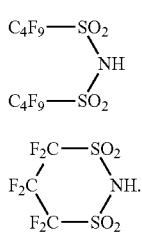
Structural Formula (C)

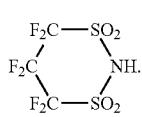
Structural Formula (D)

<14> A magnetic recording medium, including:
a non-magnetic support; and
at least a magnetic layer on or above the non-magnetic support,
wherein the magnetic layer contains the lubricating agent according to any one of <1> to <13>.

<15> An ionic liquid,
wherein the ionic liquid is formed from a Bronsted acid (HX) and a Bronsted base (B),
wherein the Bronsted base has a linear hydrocarbon group having 10 or more carbon atoms, and
wherein a difference between a pKa value of the Bronsted acid in water and a pKa value of the Bronsted base in water is 12 or more.

<16> The ionic liquid according to <15>, wherein the ionic liquid is represented by the following General Formula (1):

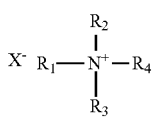
General Formula (1)

wherein at least one of $R_1$, $R_2$, $R_3$, and $R_4$ is a hydrogen atom, and at least one of $R_1$, $R_2$, $R_3$, and $R_4$ is a group which contains the linear hydrocarbon group having 10 or more carbon atoms.

<17> The ionic liquid according to <15>, wherein the Bronsted base is a cyclic amidine which contains the linear hydrocarbon group having 10 or more carbon atoms.

<18> The ionic liquid according to <17>, wherein the ionic liquid is represented by the following General Formula (2):

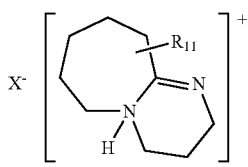
General Formula (2)

wherein $R_{11}$ denotes the linear hydrocarbon group having 10 or more carbon atoms and being attached to a carbon atom in a bicyclo ring.

<19> The ionic liquid according to any one of <15> to <18>, wherein the Bronsted acid is sulfonic acid.

<20> The ionic liquid according to any one of <15> to <19>, wherein the ionic liquid has an exothermic peak temperature determined by a differential thermal analysis (DTA) measurement of 370° C. or higher.

<21> The ionic liquid according to any one of <15> to <20>, wherein the hydrocarbon group is an alkyl group.

<22> The ionic liquid according to any one of <15> to <21>, wherein the Bronsted base is octadecylamine ($C_{18}H_{37}NH_2$), decylamine ($C_{10}H_{21}NH_2$), tetradecylamine ($C_{14}H_{29}NH_2$), eicosylamine ($C_{20}H_{41}NH_2$), oleylamine ($C_{18}H_{35}NH_2$), 2-heptylundecylamine ($CH_3(CH_2)_nCH(C_7H_{15})NH_2$), or a compound represented by the following Structural Formula (1):

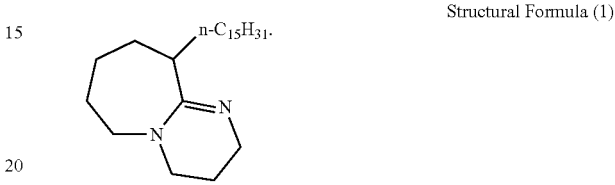
Structural Formula (1)

<23> An ionic liquid,
wherein the ionic liquid is formed from a Bronsted acid (HX) and a Bronsted base (B),
wherein the Bronsted base has a linear hydrocarbon group having 10 or more carbon atoms, and
wherein a difference between a pKa value of the Bronsted acid in acetonitrile and a pKa value of the Bronsted base in acetonitrile is 6 or more.

<24> The ionic liquid according to <23>, wherein the ionic liquid is represented by the following General Formula (1):

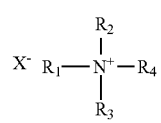
General Formula (1)

wherein at least one of $R_1$, $R_2$, $R_3$, and $R_4$ is a hydrogen atom, and at least one of $R_1$, $R_2$, $R_3$, and $R_4$ is a group which contains the linear hydrocarbon group having 10 or more carbon atoms.

<25> The ionic liquid according to <23>, wherein the Bronsted base is a cyclic amidine which contains a linear hydrocarbon group having 10 or more carbon atoms or a cyclic guanidine which contains the linear hydrocarbon group having 10 or more carbon atoms.

<26> The ionic liquid according to <25>, wherein the ionic liquid is represented by the following General Formula (2) or (3):

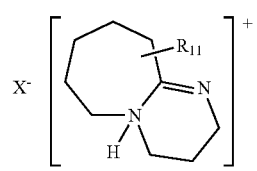
General Formula (2)

wherein $R_{11}$ denotes the linear hydrocarbon group having 10 or more carbon atoms and being attached to a carbon atom in a bicyclo ring,

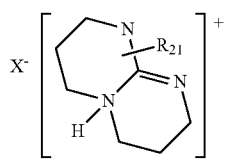

General Formula (3)

wherein $R_{21}$ denotes the linear hydrocarbon group having 10 or more carbon atoms and being attached to a carbon atom or a nitrogen atom in a bicyclo ring.

<27> The ionic liquid according to any one of <23> to <26>, wherein the ionic liquid has an exothermic peak temperature determined by a differential thermal analysis (DTA) measurement of 370° C. or higher.

<28> The ionic liquid according to any one of <23> to <27>, wherein the Bronsted acid is perfluoroalkyl sulfonic acid, a compound represented by the following Structural Formula (A), a compound represented by the following Structural Formula (B), a compound represented by the following Structural Formula (C), or a compound represented by the following Structural Formula (D):

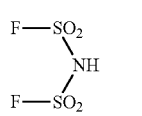

Structural Formula (A)

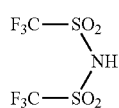

Structural Formula (B)

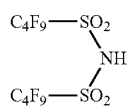

Structural Formula (C)

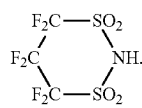

Structural Formula (D)

<29> The ionic liquid according to any one of <23> to <28>, wherein the Bronsted base is octadecylamine ($C_{18}H_{37}NH_2$), decylamine ($C_{10}H_{21}NH_2$), tetradecylamine ($C_{14}H_{29}NH_2$), eicosylamine ($C_{20}H_{41}NH_2$), oleylamine ($C_{18}H_{35}NH_2$), 2-heptylundecylamine ($CH_3(CH_2)_nCH(C_7H_{15})NH_2$), a compound represented by the following Structural Formula (2), or a compound represented by the following Structural Formula (3):

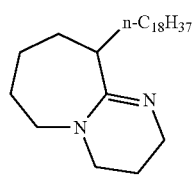

Structural Formula (2)

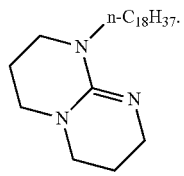

Structural Formula (3)

Advantageous Effects of the Invention

The present invention can improve a lubricating agent in thermal stability against, for example, evaporation and thermal decomposition, and can maintain an excellent lubricating property for a long period of time. Also, when the lubricating agent is used in a magnetic recording medium, the present invention can achieve the lubricating agent having the excellent lubricating property and an improved practical characteristic such as runnability, wear resistance, and durability.

DESCRIPTION OF EMBODIMENTS

Figure 1:
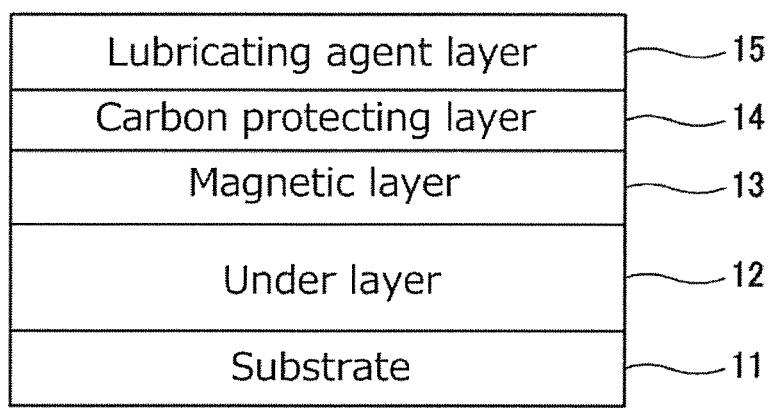
FIG. 1 is a cross-sectional view illustrating one exemplary hard disk according to one embodiment of the present invention.

Hereinafter, embodiments of the present invention will be described in detail with reference to figures in the following order.
1. Lubricating agent and ionic liquid
2. Magnetic recording medium
3. Examples 1. Lubricating Agent and Ionic Liquid A lubricating agent given as one embodiment of the present invention contains an ionic liquid represented by the general formula $X^-B^+$, and uses, as a Bronsted base (B), a compound containing a linear hydrocarbon group preferably having 10 or more carbon atoms (e.g., ammonium salt).

An ionic liquid in embodiments of the present invention is a protic ionic liquid synthesized through neutralization between a Bronsted acid (HX) and a Bronsted base (B).

This ionic liquid can exert an excellent thermal stability resulting from a difference between a pKa value of the Bronsted acid in water and a pKa value of the Bronsted base in water ($\Delta$pKa: pKa value of Bronsted base minus pKa value of Bronsted acid) of 12 or more.

The ionic liquid can also exert an excellent thermal stability resulting from a difference between a pKa value of the Bronsted acid in acetonitrile and a pKa value of the Bronsted base in acetonitrile ($\Delta$pKa: pKa value of Bronsted base minus pKa value of Bronsted acid) of 6 or more. Note that, the pKa values in acetonitrile is described in, for example, Blackwell Scientific Publications, Oxford, 1990, and J. Org. Chem. 2011, Vol. 76, pp. 391-395.

Watanabe et al. have reported that proton transferability and thermal stability of a protic ionic liquid greatly depend on $\Delta$pKa, and, therefore, when DBU (1,8-diazabicyclo[5.4.0]undec-7-ene) is used as a base, the ionic liquid is greatly improved in the thermal stability by using an acid having a pKa value so as to give the $\Delta$pKa of 15 or more (Miran, M. S., Kinoshita, H., Yasuda, T., Susan, M. A. B. H., Watanabe, M., Physicochemical Properties Determined by $\Delta$pKa for Protic Ionic Liquids Based on an Organic Superstrong Base with Various Bronsted Acids, Phys. Chem. Chem. Phys., Vol 14, pp. 5178-5186 (2012)).

However, it has not been sufficiently discussed what level of $\Delta$pKa is required for a certain application.

The present inventors conducted extensive studies and have found that thermal stability mechanisms are different depending on the numerical values of $\Delta$pKa. It has been confirmed by TG/DTA analysis that, in the case of small $\Delta$pKa, weight loss of the ionic liquid is endothermic and due to evaporation, while, in the case of large $\Delta$pKa, weight loss of the ionic liquid is exothermic and predominantly due to thermal decomposition.

Accordingly, the present inventors found that an ionic liquid having a difference between a pKa value of a Bronsted acid in water and a pKa value of a Bronsted base in water ($\Delta$pKa: pKa value of Bronsted base minus pKa value of Bronsted acid) of 12 or more exerts an excellent thermal stability and is useful as a lubricating agent.

The present inventors also found that an ionic liquid having a difference between a pKa value of a Bronsted acid in acetonitrile and a pKa value of a Bronsted base in acetonitrile ($\Delta$pKa: pKa value of Bronsted base minus pKa value of Bronsted acid) of 6 or more exerts an excellent thermal stability and is useful as a lubricating agent.

As used herein, pKa refers to an acid dissociation constant, i.e., an acid dissociation constant in water or an acid dissociation constant in acetonitrile.

The acid dissociation constant in water can be measured, for example, with reference to the method described in J. Chem. Res., Synop. 1994, 212-213. Specifically, it can be measured by a combination of a spectrometer with potentiometry.

Although the acid dissociation constant in acetonitrile is not described herein because it is described in J. Org. Chem. 1998, 63, p. 7868 or J. Org. Chem. 1997, 62, p. 8479, it can be obtained by dissolving an acid in acetonitrile, titrating the resultant with a base, and measuring a spectrum by means of a UV-vis spectrometer.

The ionic liquid has an excellent solubility in a highly volatile solvent such as lower alcohols (alcohols containing 1 to 3 carbon atoms) and ethers. Therefore, the ionic liquid can be easily formed into a solution when it is used. Also, the solvent can be easily removed when the solution is applied and used.

A compound of the present invention has a long chain alkyl group. Therefore, it has a relatively high melting point, can be produced through recrystallization, and can be very easily produced.

An exothermic peak temperature of the ionic liquid determined by a differential thermal analysis (DTA) measurement is not particularly limited and may be appropriately selected depending on the intended purpose, but is preferably 370° C. or higher, more preferably 400° C. to 500° C. from the viewpoint of exerting excellent thermal stability.

The differential thermal analysis can be performed, for example, as follows.

The measurement is performed in a temperature range of 30° C. to 600° C. at a heating rate of 10° C./min while introducing air at a flow rate of 200 mL/min using EXSTAR 6000 (manufactured by Seiko Instruments Inc.). As a gas chromatography mass spectrometer, 6890/5975 MSD (manufactured by Agilent Technologies, Inc.) was used. The following measurement conditions are used: column: DB-1 (15 m, diameter: 0.25 mm, membrane thickness: 0.1 μm); injection temperature: 280° C.; column temperature: initial temperature of 40° C., hold for 5 min, heated to 340° C. at the heating rate of 20° C./min, and hold at the same temperature; mass spectrometric unit: 5975MSD; MS detection mode: EI$^+$; quadrupole temperature: 150° C.; ion source temperature: 300° C.; mass scanning range: m/z 33-700; and calibration: PFTBA.

The upper limit of the $\Delta$pKa in water is not particularly limited and may be appropriately selected depending on the intended purpose, but the $\Delta$pKa in water is preferably 25 or less, more preferably 21 or less.

The upper limit of the $\Delta$pKa in acetonitrile is not particularly limited and may be appropriately selected depending on the intended purpose, but the $\Delta$pKa in acetonitrile is preferably 40 or less, more preferably 35 or less.

The Bronsted acid satisfying the following condition is used: the difference between the pKa value of the Bronsted acid (HX) in water and the pKa value of the Bronsted base (B) in water is 12 or more.

Also, the Bronsted acid satisfying the following condition is used: the difference between the pKa value of the Bronsted acid (HX) in acetonitrile and the pKa value of the Bronsted base (B) in acetonitrile is 6 or more.

Such Bronsted acid may be a super acid described in J. Org. Chem. 2005, Vol. 70, p. 1019. Preferably, Bronsted acids (HX) having a small pKa are used such as sulfonylimides (e.g., bis((trifluoromethyl)sulfonyl)imide (($CF_3SO_2)_2NH$), bis(nonafluorobutylsulfonyl)imide, and cyclohexafluoropropane-1,3-bis(sulfonyl)) and sulfonic acids (e.g., trifluoromethane sulfonic acid ($CF_3SO_3H$), sulfuric acid ($H_2SO_4$), methane sulfonic acid ($CH_3SO_3H$), and perfluorooctane sulfonic acid ($C_8F_{17}SO_3H$)).

In addition, the Bronsted acid may be perfluoroalkyl sulfonic acid, a compound represented by the following Structural Formula (A), a compound represented by the following Structural Formula (B), a compound represented by the following Structural Formula (C), or a compound represented by the following Structural Formula (D):

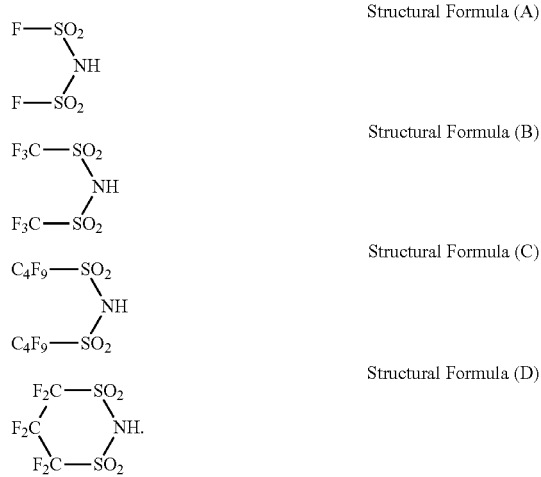

The Bronsted acid may also be organic acids described in Table 1 in the following non-patent literature: Agnes Kutt, Toomas Rodima, Jaan Saame, Elin Raamat, Vahur Maemets, Ivari Kaljurand, Ilmar A. Koppel, Romute Yu. Garlyauskayte, Yurii L. Yagupolskii, Lev M. Yagupolskii, Eduard Bernhardt, Helge Willner, and Ivo Leito, "Equilibrium Acidities of Superacids", J. Org. Chem. 2011, Vol. 76, pp. 391-395.

The pKa of the Bronsted acid in water is not particularly limited and may be appropriately selected depending on the intended purpose, but is preferably −18 to −3.

The pKa of the Bronsted acid in acetonitrile is not particularly limited and may be appropriately selected depending on the intended purpose, but is preferably −5 to −12.

An organic base compound satisfying the condition that the difference between the pKa value of the Bronsted acid (HX) in water and the pKa value of the Bronsted base (B) in water (ΔpKa) is 12 or more and containing a linear hydrocarbon group preferably having 10 or more carbon atoms (e.g., ammonium salt) may be used as the Bronsted base. The long hydrocarbon chain thereof enables a reduced coefficient of friction and an improved lubricating property.

An organic base compound satisfying the condition that the difference between the pKa value of the Bronsted acid (HX) in acetonitrile and the pKa value of the Bronsted base (B) in acetonitrile (ΔpKa) is 6 or more and containing a linear hydrocarbon group preferably having 10 or more carbon atoms (e.g., ammonium salt) may be used as the Bronsted base. The long hydrocarbon chain thereof enables a reduced coefficient of friction and an improved lubricating property.

The organic base compound is preferably a compound having a high pKa.

Examples of the organic base compound includes amines, hydroxyamines, imines, oximes, hydrazines, hydrazones, guanidine, amidines, sulfoamide, imides, amides, thioamides, carbamates, nitriles, ureas, urethanes, and cyclic heterocycles. Examples of the cyclic heterocycles include pyrrole, indole, azole, oxazole, triazole, tetrazole, and imidazole.

The Bronsted acid may also be organic bases described in Table 1 in the following non-patent literature: Ivari Kaljurand, Agnes Kuett, Lilli Soovaeli, Toomas Rodima, Vahur Maeemets, Ivo Leito, and Ilmar A. Koppel, "Extension of the Self-Consistent Spectrophotometric Basicity Scale in Acetonitrile to a Full Span of 28 pKa Units: Unification of Different Basicity Scales" J. Org. Chem. 2005, Vol. 70, pp. 1019-1028.

The upper limit of the number of carbon atoms in the linear hydrocarbon group having 10 or more carbon atoms is not particularly limited and may be appropriately selected depending on the intended purpose. However, the number of carbon atoms is preferably 25 or less, more preferably 20 or less from the viewpoint of raw material procurement.

The hydrocarbon group may be a saturated hydrocarbon group, an unsaturated hydrocarbon group having a double bond, or an unsaturated branched hydrocarbon group having a branch, as long as it is linear. Among them, the hydrocarbon group is preferably an alkyl group which is the saturated hydrocarbon group from the viewpoint of wear resistance. A linear hydrocarbon group having no branch is also preferable.

The pKa value of the Bronsted base in water is not particularly limited and may be appropriately selected depending on the intended purpose, but is preferably 9 to 30.

The pKa value of the Bronsted base in acetonitrile is not particularly limited and may be appropriately selected depending on the intended purpose, but is preferably 15 to 35.

Example of the Bronsted base includes a compound containing a nitrogen which is positively charged when it forms an ion pair with the Bronsted acid. Examples of such compound include amines, hydroxylamines, imines, oximes, hydrazines, hydrazones, guanidine, amidines, sulfoamide, imides, amides, thioamides, carbamates, nitriles, ureas, urethanes, and cyclic heterocycles. Examples of the cyclic heterocycles include pyrrole, indole, azole, oxazole, triazole, tetrazole, and imidazole, as well as the aliphatic amine, an aromatic amine, a cyclic amine, and amidine. Examples of the aliphatic amine includes a primary aliphatic amine, a secondary aliphatic amine, and a tertiary aliphatic amine. Examples of the aromatic amine includes aniline, diphenylamine, and 4-aminopyridine. Examples of the cyclic amine includes pyrrolidone, 2,2,6,6-tetramethylpiperidine, and quinuclidine. Examples of the amidine includes a cyclic amidine.

Specific examples of preferable Bronsted base include aliphatic amines such as octadecylamine ($C_{18}H_{37}NH_2$), decylamine ($C_{10}H_{21}NH_2$), tetradecylamine ($C_{14}H_{29}NH_2$), eicosylamine ($C_{20}H_{41}NH_2$), oleylamine ($C_{18}H_{35}NH_2$), and 2-heptylundecylamine ($CH_3(CH_2)_nCH(C_7H_{15})NH_2$). It is needless to say that the structure of the amines are not limited thereto. For example, the amines may be those in which a hydrocarbon chain is introduced into a heterocyclic compound, an alicyclic compound, or an aromatic compound. Additionally, a compound represented by the following Structural Formula (1), a compound represented by the following Structural Formula (2), and a compound represented by the following Structural Formula (3) are also preferably used.

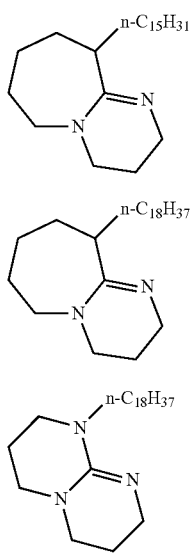

Structural Formula (1)

Structural Formula (2)

Structural Formula (3)

An ionic liquid containing the aliphatic amine as the Bronsted base is represented by the following General Formula (1):

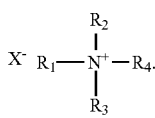

General Formula (1)

In General Formula (1), at least of $R_1$, $R_2$, $R_3$, and $R_4$ is a hydrogen atom, and at least one of $R_1$, $R_2$, $R_3$, and $R_4$ is a group which contains a linear hydrocarbon group having 10 or more carbon atoms. R group other than the linear hydrocarbon group having 10 or more carbon atoms is preferably a branched hydrocarbon, an aromatic ring, an alicycle, a hydrocarbon having an unsaturated bond, or hydrogen. Alternatively, the R group may be a heterocyclic compound or those having a substituted halogen.

The group which contains a linear hydrocarbon group having 10 or more carbon atoms is preferably a linear hydrocarbon group having 10 or more carbon atoms.

The ionic liquid is preferably one in which the Bronsted base is a cyclic amidine which contains a linear hydrocarbon group having 10 or more carbon atoms or a cyclic guanidine which contains a linear hydrocarbon group having 10 or more carbon atoms. Examples of the cyclic amidine include imidazole, benzimidazole, 1,8-diazabicyclo(5,4,0)-undecene-7 (DBU), and 1,5-diazabicyclo(4,3,0)-nonene-5 (DBN). Note that, the pKa value of imidazole is 14, the pKa value of DBU in water is 12.5, and the pKa value of DBN in water is 12.7. Examples of the cyclic guanidine include 1,5,7-triazabicyclo[4.4.0]-5-decene (TBD). A compound referred to as a super base described in Chem. Eur. J. 2012, Vol. 18, p. 3621 or J. Org. Chem. 2005, Vol. 70, p. 1019 may be used as the Bronsted base.

The ionic liquid is preferably a compound represented by the following General Formula (2), more preferably a compound represented by the following General Formula (2-1).

The ionic liquid is preferably a compound represented by the following General Formula (3), more preferably a compound represented by the following General Formula (3-1).

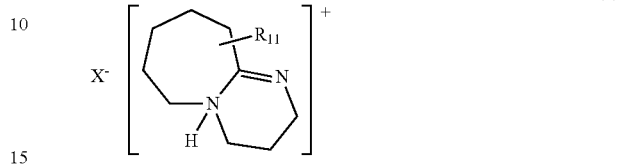

General Formula (2)

In the General Formula (2), $R_{11}$ denotes a linear hydrocarbon group having 10 or more carbon atoms and being attached to a carbon atom in a bicyclo ring.

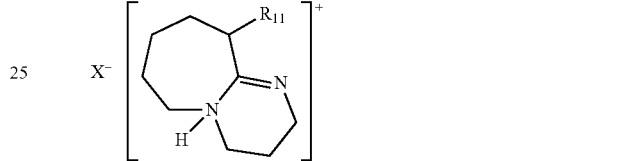

General Formula (2-1)

In the General Formula (2-1), $R_{11}$ denotes a linear hydrocarbon group having 10 or more carbon atoms.

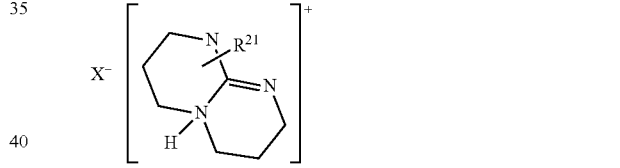

General Formula (3)

In the General Formula (3), $R_{21}$ denotes a linear hydrocarbon group having 10 or more carbon atoms and being attached to a carbon atom or a nitrogen atom in a bicyclo ring.

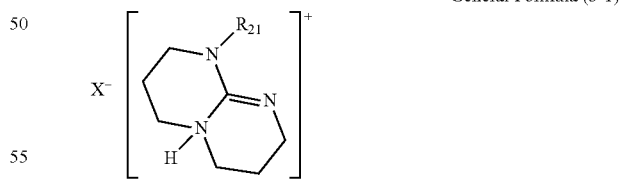

General Formula (3-1)

In the General Formula (3-1), $R_{21}$ denotes a linear hydrocarbon group having 10 or more carbon atoms.

Hereinafter, one exemplary synthetic method of the ionic liquid will be described. The ionic liquid is synthesized from the Bronsted acid and the Bronsted base. Specifically, the ionic liquid is obtained by mixing, for example, sulfonic acid with an equal amount of an organic base compound to neutralize them.

Alternatively, the ionic liquid can be obtained by neutralizing an aliphatic amine with nitric acid to produce an ammonium nitrate salt, followed by anion exchange. For example, the ionic liquid can be obtained by anion exchange of ammonium nitrate salt with an equal amount of bis(trifluoromethanesulfonyl)amide lithium salt (Li[(CF$_3$SO$_2$)$_2$N]), as represented by the following Reaction Scheme (2).

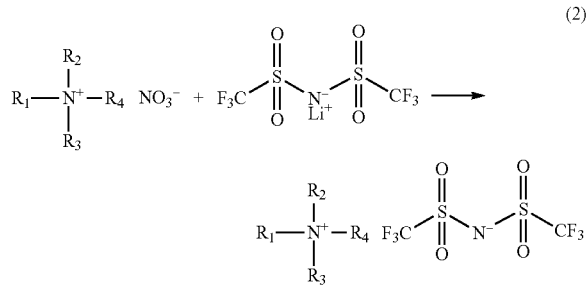

(2)

The lubricating agent in the present embodiment may contain the aforementioned ionic liquid alone or in combination with conventionally known lubricating agents. For example, the ionic liquid may be combined with a long chain carboxylic acid, a long chain carboxylic acid ester, perfluoroalkyl carboxylic acid ester, carboxylic acid perfluoroalkyl ester, perfluoroalkyl carboxylic acid perfluoroalkyl ester, or a perfluoropolyether derivative.

In order to keep a lubricating effect under a harsh condition, an extreme pressure agent may be used in combination in a compounding ratio of 30:70 to 70:30 by mass. When partial metal-to-metal contact occurs in a boundary-lubrication area, the extreme pressure agent reacts with a metal surface by the action of frictional heat generated accompanying the contact to thereby form a reaction product film. Thus, the extreme pressure agent exerts an abrasion and wear prevention effect. The extreme pressure agent may be any of, for example, a phosphorus-based extreme pressure agent, a sulfur-based extreme pressure agent, a halogen-based extreme pressure agent, an organic metal-based extreme pressure agent, and a complex type extreme pressure agent.

An anti-rust agent may be used in combination, if necessary. The anti-rust agent may be those being commonly available as an anti-rust agent for this type of magnetic recording medium. Examples thereof include phenols, naphthols, quinones, a nitrogen-containing heterocyclic compound, an oxygen-containing heterocyclic compound, and a sulfur-containing heterocyclic compound. The anti-rust agent may be mixed with the lubricating agent. Alternatively, the anti-rust agent and the lubricating agent may be deposited separately in two or more layer by, for example, forming a magnetic layer on a non-magnetic support, applying an anti-rust agent layer thereon, followed by applying a lubricating agent layer thereon.

A solvent for the lubricating agent may be alcohol-based solvents such as isopropyl alcohol (IPA) and ethanol, which may be used alone or in combination. For example, hydrocarbon-based solvents such as n-hexane or fluorosolvents may be used in combination therewith.

2. Magnetic Recording Medium

Next, a magnetic recording medium containing the aforementioned lubricating agent will now be described. A magnetic recording medium given as one embodiment of the present invention includes a non-magnetic support and a magnetic layer thereon, and the magnetic layer contains the aforementioned lubricating agent.

The lubricating agent in the present embodiment can be applied to a magnetic recording medium formed by depositing the magnetic layer on a surface of the non-magnetic support by a technique such as vapor deposition and sputtering, which is the so-called metallic thin film type magnetic recording medium. Additionally, the lubricating agent can be applied to a magnetic recording medium having a configuration in which an under layer is interposed between the non-magnetic support and the magnetic layer. Examples of such magnetic recording medium include a magnetic disk and a magnetic tape.

FIG. 1 is a cross-sectional view illustrating one exemplary hard disk. This hard disk has a configuration in which a substrate 11, an under layer 12, a magnetic layer 13, a carbon protecting layer 14, and a lubricating agent layer 15 are sequentially laminated.

Figure 2:
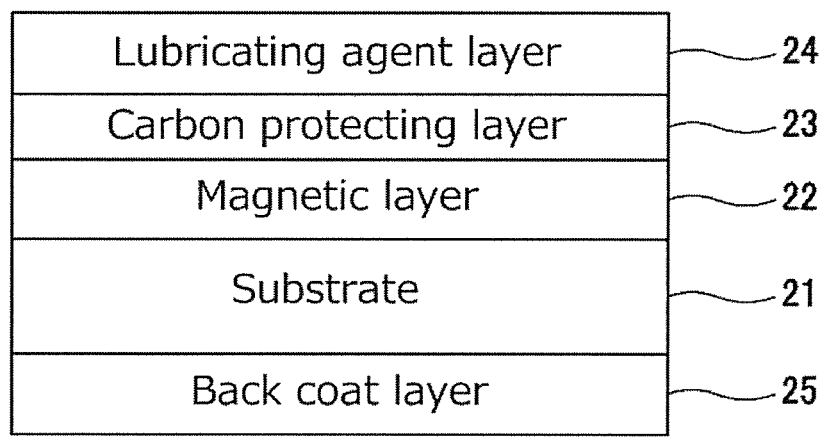
FIG. 2 is a cross-sectional view illustrating one exemplary magnetic tape according to one embodiment of the present invention.
Figure 3:
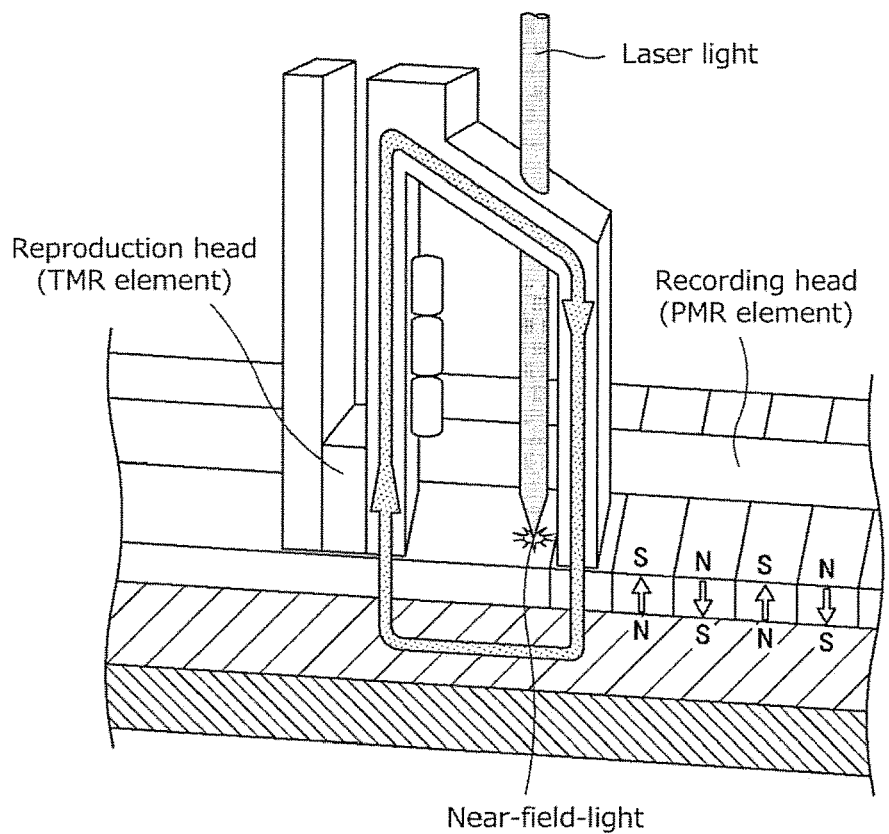
FIG. 3 is a schematic view illustrating heat assisted magnetic recording.

FIG. 2 is a cross-sectional view illustrating one exemplary magnetic tape. This magnetic tape has a configuration in which a back coat layer 25, a substrate 21, a magnetic layer 22, a carbon protecting layer 23, and a lubricating agent layer 24 are sequentially laminated.

In the magnetic disk illustrated in FIG. 1, the non-magnetic support corresponds to the substrate 11 and the under layer 12. In the magnetic tape illustrated in FIG. 2, the non-magnetic support corresponds to the substrate 21. In the case where a rigid substrate such as an Al alloy plate and a glass plate is used as the non-magnetic support, a surface of the substrate may be made hard by forming an oxide film (for example, through an alumite treatment) or a Ni—P film thereon.

The magnetic layers 13 and 22 are formed as continuous films by a technique such as plating, sputtering, vacuum deposition, and plasma CVD. Examples of the magnetic layers 13 and 22 include an in-plane magnetization recording metallic magnetic film consisting of, for example, a metal (e.g., Fe, Co, or Ni), a Co—Ni based alloy, a Co—Pt based alloy, a Co—Ni—Pt based alloy, a Fe—Co based alloy, a Fe—Ni based alloy, a Fe—Co—Ni based alloy, a Fe—Ni—B based alloy, a Fe—Co—B based alloy, and a Fe—Co—Ni—B based alloy; and a perpendicular magnetization recording metallic magnetic film such as a Co—Cr based alloy film and a Co—O based film.

In particular, in the case where the in-plane magnetization recording metallic magnetic film is formed, orientation may be eliminated, planar isotropy may be ensured, and coercive force may be improved as follows. A non-magnetic material (e.g., Bi, Sb, Pb, Sn, Ga, In, Ge, Si, and Tl) is formed as the under layer 12 on the non-magnetic support in advance, and a metallic magnetic material is vertically vapor-deposited or sputtered thereon to thereby disperse the non-magnetic material into the magnetic metallic thin film.

Hard protecting layers 14 and 23 (e.g., a carbon film, a diamond-like carbon film, a chromium oxide film, or SiO$_2$ film) may be formed on surfaces of the magnetic layers 13 and 22.

Example of a method for allowing the aforementioned lubricating agent to be contained in such metallic thin film type magnetic recording medium includes a method in which the lubricating agent is applied, as a top coat, onto surfaces of the magnetic layers 13 and 22 or surfaces of the protecting layers 14 and 23, as illustrated in FIGS. 1 and 2. An amount of the lubricating agent to be applied is preferably 0.1 mg/m$^2$~100 mg/m$^2$, more preferably 0.5 m g/m$^2$~30 mg/m$^2$, particularly preferably 0.5 mg/m$^2$~20 mg/m$^2$.

As illustrated in FIG. 2, the metallic thin film type magnetic tape may contain a back coat layer 25, if necessary, in addition to the magnetic layer 22 serving as the metallic magnetic thin film.

The back coat layer 25 is formed by adding carbon-based powder for imparting electroconductivity and an inorganic pigment for controlling surface roughness to a resin binder, followed by applying. In the present embodiment, the aforementioned lubricating agent may be internally added or contained as the top coat in the back coat layer 25. Alternatively, the aforementioned lubricating agent may be internally added or contained as the top coat in the magnetic layer 22 and the back coat layer 25.

In another embodiment, the lubricating agent can be applied to a magnetic recording medium in which magnetic paint is applied onto a surface of the non-magnetic support to thereby form a magnetic coating film serving as the magnetic layer, which is the so-called coating type magnetic recording medium. In the coating type magnetic recording medium, any conventionally known resin binder and magnetic powder constituting the non-magnetic support or the magnetic coating film can be used.

Examples of the non-magnetic support include a polymeric support formed of, for example, a polymeric material such as polyesters, polyolefins, cellulose derivatives, vinyl-based resins, polyimides, polyamides, and polycarbonates; a metallic substrate formed of, for example, aluminium alloy or titanium alloy; a ceramic substrate formed of, for example, alumina glass; and a glass substrate. The shape thereof is not particularly limited, and may be any shape such as a tape-like shape, a sheet-like shape, or a drum-like shape. In addition, the non-magnetic support may be surface-treated to form fine unevenness in order to control its surface nature.

Examples of the magnetic powder include ferromagnetic iron oxide-based particles (e.g., $\gamma$-$Fe_2O_3$ and cobalt-coated $\gamma$-$Fe_2O_3$), ferromagnetic chromium dioxide-based particles, ferromagnetic metal-based particles consisting of a metal (e.g., Fe, Co, and Ni) or alloy containing it, and hexagonal crystal-based ferrite particles having a hexagonal-plate-like shape.

Examples of the resin binder include a polymer such as vinyl chloride, vinyl acetate, vinyl alcohol, vinylidene chloride, acrylic ester, methacrylic ester, styrene, butadiene, and acrylonitrile; a copolymer of any two or more of these polymers; a polyurethane resin, a polyester resin, and an epoxy resin. In order to improve dispersibility of the magnetic powder, a hydrophilic polar group such as a carboxylic acid group, a carboxyl group, or a phosphate group may be introduced into the binder.

The magnetic coating film may contain an additive such as a dispersing agent, an abrasive agent, an antistatic agent, and an anti-rust agent, in addition to the magnetic powder and the resin binder.

Examples of a method for allowing the aforementioned lubricating agent to be contained in such coating type magnetic recording medium includes a method in which the lubricating agent is internally added to the magnetic layer constituting the magnetic coating film formed on the non-magnetic support, a method in which the lubricating agent is deposited onto a surface of the magnetic layer as the top coat, and a combination thereof. In the case where the lubricating agent is internally added to the magnetic coating film, the lubricating agent is added in the amount of 0.2 parts by mass to 20 parts by mass relative to 100 parts by mass of the resin binder.

In the case where the lubricating agent is deposited onto a surface of the magnetic layer as the top coat, the lubricating agent is preferably applied in the amount of 0.1 mg/m$^2$ to 100 mg/m$^2$, more preferably 0.5 m g/m$^2$ to 20 mg/m$^2$. Note that, a method for depositing the lubricating agent as the top coat may be a method in which the ionic liquid is dissolved in a solvent, and then the resultant solution is applied or sprayed, or a magnetic recording medium is immersed into the solution.

In the present embodiment, a lubricating agent containing an ionic liquid which is formed from a Bronsted acid and a Bronsted base containing a linear hydrocarbon group preferably having 10 or more carbon atoms and which has a difference of pKa values thereof ($\Delta$pKa) in water is 12 or more can exert a good lubricating effect to thereby reduce a coefficient of friction and achieve thermally high stability. The lubricating effect is not impaired even under a harsh condition such as high temperature, low temperature, high humidity, or low humidity.

In the present embodiment, a lubricating agent containing an ionic liquid which is formed from a Bronsted acid and a Bronsted base containing a linear hydrocarbon group preferably having 10 or more carbon atoms and which has a difference of pKa values thereof ($\Delta$pKa) in acetonitrile is 6 or more can exert a good lubricating effect to thereby reduce a coefficient of friction and achieve thermally high stability. The lubricating effect is not impaired even under a harsh condition such as high temperature, low temperature, high humidity, or low humidity.

Thus, the magnetic recording medium to which the lubricating agent in the present embodiment is applied can exert excellent runnability, wear resistance, and durability and can improve thermal stability due to its lubricating effect.

EXAMPLES

3. Example

Hereinafter, specific examples of the present invention will now be described. In Examples, ionic liquids were synthesized, and lubrication agents containing the ionic liquids were produced. Then, magnetic disks and magnetic tapes were produced using the lubrication agents, each of which was evaluated for disk durability and tape durability. Production of the magnetic disks, a disk durability test, production of the magnetic tapes, and a tape durability test were performed as follows. Note that, the present invention is not limited to Examples.

<Production of Magnetic Disk>

A magnetic disk illustrated in FIG. 1 was produced by forming a magnetic thin film on a glass substrate according to, for example, International Publication No. WO2005/068589. Specifically, a chemically strengthened glass disk consisting of aluminosilicate glass (external diameter: 65 mm, internal diameter: 20 mm, disk thickness: 0.635 mm) was prepared. A surface of the disk was polished so as to have Rmax of 4.8 nm and Ra of 0.43 nm. The glass substrate was subjected to ultrasonic cleaning in pure water and isopropyl alcohol (IPA) (purity: 99.9% or higher) for 5 min each, and then left to stand in IPA saturated vapor for 1.5 min, followed by drying, which was determined as a substrate 11.

On this substrate 11, 30 nm of a NiAl alloy (Ni: 50 mol %, Al: 50 mol %) thin film serving as a seed layer, 8 nm of a CrMo alloy (Cr: 80 mol %, Mo: 20 mol %) thin film serving as a under layer 12, and 15 nm of a CoCrPtB alloy (Co: 62 mol %, Cr: 20 mol %, Pt: 12 mol %, and B: 6 mol %) serving as a magnetic layer 13 were sequentially formed by a DC magnetron sputtering method.

Next, a 5 nm of carbon protecting layer 14 consisting of amorphous diamond-like carbon was formed by a plasma CVD method. The thus formed disk sample was subjected to ultrasonic cleaning in isopropyl alcohol (IPA) (purity: 99.9% or higher) contained in a cleaning vessel for 10 min to thereby remove contaminants on a surface of the disk, followed by drying. Then, a solution of an ionic liquid in IPA was applied onto the surface of the disk by a dip coating method under an environment of 25° C. and 50% relative humidity (RH) to thereby form an about 1 nm of a lubricating agent layer 15.

<Disk Durability Test>

A CSS durability test was performed using a commercially available strain gauge type disk friction and wear tester as follows. A hard disk was mounted on a rotary spindle with tightening torque of 14.7 Ncm, and then, a head slider was mounted on the hard disk so that the center of an air bearing surface of the head slider in an inner peripheral side was 17.5 mm apart from the center of the hard disk. The head used in this measurement was IBM 3370 type in-line head, the slider was made of $Al_2O_3$—TiC, and a head load was 63.7 mN. In this test, the maximum value of friction force was monitored every CSS (Contact, Start, Stop) under an environment of 25° C., 60% RH, and cleanliness of 100. The number of times in which a coefficient of friction exceeds 1.0 was determined as a result of the CSS durability test. In the result of the CSS durability test, when the number of times was greater than 50,000, the result was displayed as ">50,000." To examine thermal resistance, the CSS durability test was performed again in the same manner after a heating test at a temperature of 300° C. for 3 min.

<Production of Magnetic Tape>

A magnetic tape having a cross-sectional configuration as shown in FIG. 2 was produced. Firstly, Co was deposited onto a substrate 21 consisting of a MICTRON (aromatic polyamide) film having a thickness of 5 μm (manufactured by Toray Industries, Inc.) by an oblique deposition method to thereby form a magnetic layer 22 consisting of a 100 nm thick ferromagnetic metal thin film. Next, a 10 nm of carbon protecting layer 23 consisting of carbon-like carbon was formed on a surface of the ferromagnetic metal thin film by the plasma CVD method, followed by cutting to 6 mm width. The ionic liquid dissolved in IPA was applied onto the magnetic layer 22 so as to have a film thickness of about 1 nm to thereby form a lubricating agent layer 24. Thus, a sample tape was produced.

<Tape Durability Test>

For each sample tape, still durability under an environment of a temperature of −5° C. and an environment of a temperature of 40° C. and 30% RH, and a coefficient of friction and shuttle durability under an environment of a temperature of −5° C. and an environment of a temperature of 40° C. and 90% RH were measured. The still durability was evaluated as attenuation time for which the output in the pause state was decreased by −3 dB. The shuttle durability was evaluated as the number of shuttle runs before the output was decreased by 3 dB when the sample tape was subjected to repeated shuttle running operations for 2 min per run. Additionally, in order to examine thermal resistance, the durability test was performed again in the same manner after a heating test at a temperature of 100° C. for 10 min.

<3.1 Effect of Difference Between pKa Value of Bronsted Acid and pKa Value of Bronsted Base (ΔpKa)>

Ionic liquids were synthesized having different differences between pKa values of Bronsted acids and pKa values of Bronsted bases (ΔpKa). Lubricating agents containing the ionic liquids were used in magnetic recording media to examine an effect of the difference between a pKa value of a Bronsted acid and a pKa value of a Bronsted base (ΔpKa).

Note that, pKa values in Examples 1 to 35 and Comparative Examples 1 to 26 refer to pKa values in water, and pKa values in Examples 36 to 56 and Comparative Examples 27 to 32 refer to pKa values in acetonitrile.

Example 1

[Ionic Liquid 1]

As described in Table 2, bis(trifluoromethylsulfonyl)imide (pKa=−10) was used as the Bronsted acid, and octadecylamine containing a linear hydrocarbon group having 18 carbon atoms (pKa=10.7) was used as the Bronsted base. The difference between a pKa value of a Bronsted acid and a pKa value of a Bronsted base (ΔpKa) was 20.7. Ionic liquid 1 was synthesized by neutralizing octadecylamine with nitric acid to produce an ammonium nitrate salt, followed by anion exchange of the ammonium nitrate salt with an equal amount of bis(trifluoromethylsulfonyl)imide lithium salt ($Li[(CF_3SO_2)_2N]$). Note that, Ionic liquid 1 was the same compound as Ionic liquid 12 described below, and the detailed synthetic method thereof was as described in the synthetic method of Ionic liquid 12.

Example 2

[Ionic Liquid 2]

As described in Table 2, trifluoromethane sulfonic acid ($CF_3SO_3H$, pKa=−7) was used as the Bronsted acid, and octadecylamine containing a linear hydrocarbon group having 18 carbon atoms (pKa=10.7) was used as the Bronsted base. The difference between a pKa value of a Bronsted acid and a pKa value of a Bronsted base (ΔpKa) was 17.7. Ionic liquid 2 was synthesized by mixing octadecylamine with an equal amount of trifluoromethane sulfonic acid to thereby neutralize it.

Example 3

[Ionic Liquid 3]

As described in Table 2, sulfuric acid ($H_2SO_4$, pKa=−3) was used as the Bronsted acid, and octadecylamine containing a linear hydrocarbon group having 18 carbon atoms (pKa=10.7) was used as the Bronsted base. The difference between a pKa value of a Bronsted acid and a pKa value of a Bronsted base (ΔpKa) was 13.7. Ionic liquid 3 was synthesized by mixing octadecylamine with an equal amount of sulfuric acid to thereby neutralize it.

Example 4

[Ionic Liquid 4]

As described in Table 2, methane sulfonic acid ($CH_3SO_3H$, pKa=−2) was used as the Bronsted acid, and octadecylamine containing a linear hydrocarbon group having 18 carbon atoms (pKa=10.7) was used as the Bronsted base. The difference between a pKa value of a Bronsted acid and a pKa value of a Bronsted base (ΔpKa) was 12.7. Ionic liquid 4 was synthesized by mixing octadecylamine with an equal amount of trifluoromethane sulfonic acid to thereby neutralize it.

Comparative Example 1

Comparative Ionic Liquid 1

As described in Table 2, trifluoroacetic acid ($CF_3COOH$, pKa=0.5) was used as the Bronsted acid, and octadecylamine containing a linear hydrocarbon group having 18 carbon atoms (pKa=10.7) was used as the Bronsted base. The difference between a pKa value of a Bronsted acid and a pKa value of a Bronsted base (ΔpKa) was 10.2. Comparative ionic liquid 1 was synthesized by mixing octadecylamine with an equal amount of trifluoroacetic acid to thereby neutralize it.

Comparative Example 2

Comparative Ionic Liquid 2

As described in Table 2, perfluorooctanoic acid ($C_7F_{15}COOH$, pKa=2.5) was used as the Bronsted acid, and octadecylamine containing a linear hydrocarbon group having 18 carbon atoms (pKa=10.7) was used as the Bronsted base. The difference between a pKa value of a Bronsted acid and a pKa value of a Bronsted base (ΔpKa) was 8.2. Comparative ionic liquid 2 was synthesized by mixing octadecylamine with an equal amount of perfluorooctanoic acid to thereby neutralize it.

Comparative Example 3

Comparative Ionic Liquid 3

As described in Table 2, stearic acid ($C_{17}F_{35}COOH$, pKa=5.0) was used as the Bronsted acid, and octadecylamine containing a linear hydrocarbon group having 18 carbon atoms (pKa=10.7) was used as the Bronsted base. The difference between a pKa value of a Bronsted acid and a pKa value of a Bronsted base (ΔpKa) was 5.7. Comparative ionic liquid 3 was synthesized by mixing octadecylamine with an equal amount of stearic acid to thereby neutralize it.

TABLE 2

| | Structural Formula of Bronsted acid | pKa of Bronsted acid | ΔpKa |
|---|---|---|---|
| Ionic liquid 1 | 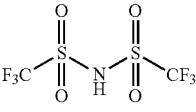 | −10 | 20.7 |
| Ionic liquid 2 | $CF_3SO_3H$ | −7 | 17.7 |
| Ionic liquid 3 | $H_2SO_4$ | −3 | 13.7 |
| Ionic liquid 4 | $CH_3SO_3H$ | −2 | 12.7 |
| Comparative ionic liquid 1 | $CF_3COOH$ | 0.5 | 10.2 |
| Comparative ionic liquid 2 | $C_7F_{15}COOH$ | 2.5 | 8.2 |
| Comparative ionic liquid 3 | $C_{17}H_{35}COOH$ | 5.0 | 5.7 |

Example 5

A magnetic disk was produced as described above using a lubricating agent containing Ionic liquid 1. As described in Table 3, the CSS measurement result of the magnetic disk was greater than 50,000, the CSS measurement result after the heating test was also greater than 50,000, indicating excellent durability.

Example 6

A magnetic disk was produced as described above using a lubricating agent containing Ionic liquid 2. As described in Table 3, the CSS measurement result of the magnetic disk was greater than 50,000, the CSS measurement result after the heating test was also greater than 50,000, indicating excellent durability.

Example 7

A magnetic disk was produced as described above using a lubricating agent containing Ionic liquid 3. As described in Table 3, the CSS measurement result of the magnetic disk was greater than 50,000, the CSS measurement result after the heating test was also greater than 50,000, indicating excellent durability.

Example 8

A magnetic disk was produced as described above using a lubricating agent containing Ionic liquid 4. As described in Table 3, the CSS measurement result of the magnetic disk was greater than 50,000, the CSS measurement result after the heating test was also greater than 50,000, indicating excellent durability.

Comparative Example 4

A magnetic disk was produced as described above using a lubricating agent containing Comparative ionic liquid 1. As described in Table 3, the CSS measurement result of the magnetic disk was greater than 50,000, but the CSS measurement result after the heating test was 1,230, indicating that the heating test deteriorated durability. It is believed that this is because high temperature allowed ionic dissociation to proceed to thereby deteriorate thermal stability.

Comparative Example 5

A magnetic disk was produced as described above using a lubricating agent containing Comparative ionic liquid 2. As described in Table 3, the CSS measurement result of the magnetic disk was greater than 50,000, but the CSS measurement result after the heating test was 891, indicating that the heating test deteriorated durability. It is believed that this is because, as with Comparative Example 4, high temperature allowed ionic dissociation to proceed to thereby deteriorate thermal stability.

Comparative Example 6

A magnetic disk was produced as described above using a lubricating agent containing Comparative ionic liquid 3. As described in Table 3, the CSS measurement result of the magnetic disk was greater than 50,000, but the CSS measurement result after the heating test was 803, indicating that the heating test deteriorated durability. It is believed that this is because, as with Comparative Example 4, high temperature allowed ionic dissociation to proceed to thereby deteriorate thermal stability.

TABLE 3

|  | Lubricating agent | CSS durability | | CSS durability after heating | |
|---|---|---|---|---|---|
| Example 5 | Ionic liquid 1 | 25° C., 60% RH | >50,000 | 25° C., 60% RH | >50,000 |
| Example 6 | Ionic liquid 2 | 25° C., 60% RH | >50,000 | 25° C., 60% RH | >50,000 |
| Example 7 | Ionic liquid 3 | 25° C., 60% RH | >50,000 | 25° C., 60% RH | >50,000 |
| Example 8 | Ionic liquid 4 | 25° C., 60% RH | >50,000 | 25° C., 60% RH | >50,000 |
| Comparative Example 4 | Comparative ionic liquid 1 | 25° C., 60% RH | >50,000 | 25° C., 60% RH | 1,230 |
| Comparative Example 5 | Comparative ionic liquid 2 | 25° C., 60% RH | >50,000 | 25° C., 60% RH | 891 |
| Comparative Example 6 | Comparative ionic liquid 3 | 25° C., 60% RH | >50,000 | 25° C., 60% RH | 803 |

Next, Examples in which Ionic liquids 1 to 4 and Comparative ionic liquids 1 to 3 were applied to magnetic tapes will now be described.

Example 9

A magnetic tape was produced as described above using the lubricating agent containing Ionic liquid 1. As described in Table 4, the coefficients of friction of the magnetic tapes after 100 times of shuttle runs were 0.19 under the environment of a temperature of −5° C. and 0.23 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 1 was applied has excellent frictional property, still durability, and shuttle durability.

Example 10

A magnetic tape was produced as described above using the lubricating agent containing Ionic liquid 2. As described in Table 4, the coefficients of friction of the magnetic tapes after 100 times of shuttle runs were 0.20 under the environment of a temperature of −5° C. and 0.23 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 2 was applied has excellent frictional property, still durability, and shuttle durability.

Example 11

A magnetic tape was produced as described above using the lubricating agent containing Ionic liquid 3. As described in Table 4, the coefficients of friction of the magnetic tapes after 100 times of shuttle runs were 0.25 under the environment of a temperature of −5° C. and 0.28 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 3 was applied has excellent frictional property, still durability, and shuttle durability.

Example 12

A magnetic tape was produced as described above using the lubricating agent containing Ionic liquid 4. As described in Table 4, the coefficients of friction of the magnetic tapes after 100 times of shuttle runs were 0.24 under the environment of a temperature of −5° C. and 0.28 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 4 was applied has excellent frictional property, still durability, and shuttle durability.

Comparative Example 7

A magnetic tape was produced as described above using the lubricating agent containing Comparative ionic liquid 1. As described in Table 4, the coefficients of friction of the magnetic tapes after 100 times of shuttle runs were 0.23 under the environment of a temperature of −5° C. and 0.30 under the environment of a temperature of 40° C. and a relative humidity of 90%. The still durabilities were 45 min under the environment of a temperature of −5° C. and 59 min under the environment of a temperature of 40° C. and a relative humidity of 30%. The shuttle durabilities were 135 times under the environment of a temperature of −5° C. and 126 times under the environment of a temperature of 40° C. and a relative humidity of 90%. The still durabilities after the heating tests were 26 min under the environment of a temperature of −5° C. and 31 min under the environment of a temperature of 40° C. and a relative humidity of 30%. The shuttle durabilities after the heating tests were 55 times under the environment of a temperature of −5° C. and 42 times under the environment of a temperature of 40° C. and a relative humidity of 90%. From these results, it has been found that the magnetic tape onto which Comparative ionic liquid 1 was applied is greatly deteriorated in the still durability after the heating test and the shuttle durability after the heating test.

Comparative Example 8

A magnetic tape was produced as described above using the lubricating agent containing Comparative ionic liquid 2. As described in Table 4, the coefficients of friction of the magnetic tapes after 100 times of shuttle runs were 0.21 under the environment of a temperature of −5° C. and 0.25 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were 12 min under the environment of a temperature of −5° C. and 16 min under the environment of a temperature of 40° C. and a relative humidity of 30%. The shuttle durabilities after the heating tests were 30 times under the environment of a temperature of −5° C. and 23 times under the environment of a temperature of 40° C. and a relative humidity of 90%. From these results, it has been found that the magnetic tape onto which Comparative ionic liquid 2 was applied is greatly deteriorated in the still durability after the heating test and the shuttle durability after the heating test.

Comparative Example 9

A magnetic tape was produced as described above using the lubricating agent containing Comparative ionic liquid 3. As described in Table 4, the coefficients of friction of the magnetic tapes after 100 times of shuttle runs were 0.21 under the environment of a temperature of −5° C. and 0.25 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were 7 min under the environment of a temperature of −5° C. and 9 min under the environment of a temperature of 40° C. and a relative humidity of 30%. The shuttle durabilities after the heating tests were 15 times under the environment of a temperature of −5° C. and 12 times under the environment of a temperature of 40° C. and a relative humidity of 90%. From these results, it has been found that the magnetic tape onto which Comparative ionic liquid 3 was applied is greatly deteriorated in the still durability after the heating test and the shuttle durability after the heating test.

TABLE 4

| | Lubricating agent | Coefficient of friction after 100 times of shuttle runs | | Still durability/min | | Shuttle durability | | Still durability after heating | | Shuttle durability after heating | |
|---|---|---|---|---|---|---|---|---|---|---|---|
| Ex. 9 | Ionic liquid 1 | −5° C. | 0.19 | −5° C. | >60 | −5° C. | >200 | −5° C. | >60 | −5° C. | >200 |
| | | 40° C., 90% RH | 0.23 | 40° C., 30% RH | >60 | 40° C., 90% RH | >200 | 40° C., 30% RH | >60 | 40° C., 90% RH | >200 |
| Ex. 10 | Ionic liquid 2 | −5° C. | 0.20 | −5° C. | >60 | −5° C. | >200 | −5° C. | >60 | −5° C. | >200 |
| | | 40° C., 90% RH | 0.23 | 40° C., 30% RH | >60 | 40° C., 90% RH | >200 | 40° C., 30% RH | >60 | 40° C., 90% RH | >200 |
| Ex. 11 | Ionic liquid 3 | −5° C. | 0.25 | −5° C. | >60 | −5° C. | >200 | −5° C. | >60 | −5° C. | >200 |
| | | 40° C., 90% RH | 0.28 | 40° C., 30% RH | >60 | 40° C., 90% RH | >200 | 40° C., 30% RH | >60 | 40° C., 90% RH | >200 |
| Ex. 12 | Ionic liquid 4 | −5° C. | 0.24 | −5° C. | >60 | −5° C. | >200 | −5° C. | >60 | −5° C. | >200 |
| | | 40° C., 90% RH | 0.28 | 40° C., 30% RH | >60 | 40° C., 90% RH | >200 | 40° C., 30% RH | >60 | 40° C., 90% RH | >200 |
| Comp. Ex. 7 | Comparative ionic liquid 1 | −5° C. | 0.23 | −5° C. | 45 | −5° C. | 135 | −5° C. | 26 | −5° C. | 55 |
| | | 40° C., 90% RH | 0.30 | 40° C., 30% RH | 59 | 40° C., 90% RH | 126 | 40° C., 30% RH | 31 | 40° C., 90% RH | 42 |

TABLE 4-continued

|  | Lubricating agent | Coefficient of friction after 100 times of shuttle runs | | Still durability/min | | Shuttle durability | | Still durability after heating | | Shuttle durability after heating | |
|---|---|---|---|---|---|---|---|---|---|---|---|
| Comp. Ex. 8 | Comparative ionic liquid 2 | −5° C.<br>40° C., 90% RH | 0.21<br>0.25 | −5° C.<br>40° C., 30% RH | >60<br>>60 | −5° C.<br>40° C., 90% RH | >200<br>>200 | −5° C.<br>40° C., 30% RH | 12<br>16 | −5° C.<br>40° C., 90% RH | 30<br>23 |
| Comp. Ex. 9 | Comparative ionic liquid 3 | −5° C.<br>40° C., 90% RH | 0.21<br>0.25 | −5° C.<br>40° C., 30% RH | >60<br>>60 | −5° C.<br>40° C., 90% RH | >200<br>>200 | −5° C.<br>40° C., 30% RH | 7<br>9 | −5° C.<br>40° C., 90% RH | 15<br>12 |

As can be seen from Tables 3 and 4, use of the ionic liquid having the difference between the pKa value of the Bronsted acid in water and the pKa value of the Bronsted base in water (ΔpKa) of 12 or more can achieve excellent thermal stability and durability.

<3.2 Effects of Number of Carbon Atoms and Structure in Linear Hydrocarbon of Bronsted Base>

Next, ionic liquids were synthesized using, as the Bronsted base, aliphatic amines having the different number of carbon atoms and structures (double bond, partially branched) in linear hydrocarbons. Lubricating agents containing the ionic liquids were used in magnetic recording media to examine effects of the number of carbon atoms and the structure in the linear hydrocarbon of the Bronsted base. Note that, Bronsted basicity of the aliphatic amine is not greatly varied depending on the length of the hydrocarbon, and the difference between a pKa value of a Bronsted acid and a pKa value of a Bronsted base (ΔpKa) was about 17 to about 18.

Example 13

[Ionic Liquid 5]
As described in Table 5, trifluoromethane sulfonic acid ($CF_3SO_3H$) was used as the Bronsted acid, and decylamine containing a linear hydrocarbon group having 10 carbon atoms ($C_{10}H_{21}NH_2$) was used as the Bronsted base. Ionic liquid 5 was synthesized by mixing decylamine with an equal amount of trifluoromethane sulfonic acid to thereby neutralize it.

Example 14

[Ionic Liquid 6]
As described in Table 5, trifluoromethane sulfonic acid ($CF_3SO_3H$) was used as the Bronsted acid, and tetradecylamine containing a linear hydrocarbon group having 14 carbon atoms ($C_{14}H_{29}NH_2$) was used as the Bronsted base. Ionic liquid 6 was synthesized by mixing tetradecylamine with an equal amount of trifluoromethane sulfonic acid to thereby neutralize it.

Example 15

[Ionic Liquid 7]
As described in Table 5, trifluoromethane sulfonic acid ($CF_3SO_3H$) was used as the Bronsted acid, and eicosylamine containing a linear hydrocarbon group having 20 carbon atoms ($C_{20}H_{41}NH_2$) was used as the Bronsted base. Ionic liquid 7 was synthesized by mixing eicosylamine with an equal amount of trifluoromethane sulfonic acid to thereby neutralize it.

Example 16

[Ionic Liquid 8]
As described in Table 5, trifluoromethane sulfonic acid ($CF_3SO_3H$) was used as the Bronsted acid, and oleylamine containing a linear hydrocarbon group having 18 carbon atoms ($C_{18}H_{35}NH_2$) was used as the Bronsted base. Ionic liquid 8 was synthesized by mixing oleylamine with an equal amount of trifluoromethane sulfonic acid to thereby neutralize it.

Example 17

[Ionic Liquid 9]
As described in Table 5, trifluoromethane sulfonic acid ($CF_3SO_3H$) was used as the Bronsted acid, and 2-heptylundecylamine containing a partially branched linear hydrocarbon group having 18 carbon atoms ($CH_3(CH_2)_n CH(C_7H_{15})$—$NH_2$) (partially branched) was used as the Bronsted base. Ionic liquid 9 was synthesized by mixing 2-heptylundecylamine with an equal amount of trifluoromethane sulfonic acid to thereby neutralize it.

Comparative Example 10

Comparative Ionic Liquid 4

As described in Table 5, trifluoromethane sulfonic acid ($CF_3SO_3H$) was used as the Bronsted acid, and octylamine containing a linear hydrocarbon group having 8 carbon atoms ($C_8H_{17}NH_2$) was used as the Bronsted base. Comparative ionic liquid 4 was synthesized by mixing octylamine with an equal amount of trifluoromethane sulfonic acid to thereby neutralize it.

Comparative Example 11

Comparative Ionic Liquid 5

As described in Table 5, trifluoromethane sulfonic acid ($CF_3SO_3H$) was used as the Bronsted acid, and isobutylamine containing a linear hydrocarbon group having 4 carbon atoms ($C_4H_9NH_2$) was used as the Bronsted base. Comparative ionic liquid 4 was synthesized by mixing isobutylamine with an equal amount of trifluoromethane sulfonic acid to thereby neutralize it.

TABLE 5

| Lubricating agent | Aliphatic amine | Total number of carbon atoms |
|---|---|---|
| Ionic liquid 5 | $C_{10}H_{21}NH_2$ | 10 |
| Ionic liquid 6 | $C_{14}H_{29}NH_2$ | 14 |

TABLE 5-continued

| Lubricating agent | Aliphatic amine | Total number of carbon atoms |
|---|---|---|
| Ionic liquid 7 | $C_{20}H_{41}NH_2$ | 20 |
| Ionic liquid 8 | $C_{18}H_{35}NH_2$ | 18 |
| Ionic liquid 9 | iso-$C_{18}H_{37}NH_2$ | 18 |
| Comparative ionic liquid 4 | $C_8H_{17}NH_2$ | 8 |
| Comparative ionic liquid 5 | $C_4H_9NH_2$ | 4 |

Example 18

A magnetic disk was produced as described above using a lubricating agent containing Ionic liquid 5. As described in Table 6, the CSS measurement result of the magnetic disk was greater than 50,000, indicating excellent durability.

Example 19

A magnetic disk was produced as described above using a lubricating agent containing Ionic liquid 6. As described in Table 6, the CSS measurement result of the magnetic disk was greater than 50,000, indicating excellent durability.

Example 20

A magnetic disk was produced as described above using a lubricating agent containing Ionic liquid 7. As described in Table 6, the CSS measurement result of the magnetic disk was greater than 50,000, indicating excellent durability.

Example 21

A magnetic disk was produced as described above using a lubricating agent containing Ionic liquid 8. As described in Table 6, the CSS measurement result of the magnetic disk was greater than 50,000, indicating excellent durability.

Example 21

A magnetic disk was produced as described above using a lubricating agent containing Ionic liquid 9. As described in Table 6, the CSS measurement result of the magnetic disk was greater than 50,000, indicating excellent durability.

Comparative Example 12

A magnetic disk was produced as described above using a lubricating agent containing Comparative Ionic liquid 4. As described in Table 6, the CSS measurement result of the magnetic disk was 23,500.

Comparative Example 13

A magnetic disk was produced as described above using a lubricating agent containing Comparative Ionic liquid 5. As described in Table 6, the CSS measurement result of the magnetic disk was 11,000.

TABLE 6

|  | Lubricating agent | CSS durability |  |
|---|---|---|---|
| Example 18 | Ionic liquid 5 | 25° C., 60% RH | >50,000 |
| Example 19 | Ionic liquid 6 | 25° C., 60% RH | >50,000 |
| Example 20 | Ionic liquid 7 | 25° C., 60% RH | >50,000 |
| Example 21 | Ionic liquid 8 | 25° C., 60% RH | >50,000 |
| Example 22 | Ionic liquid 9 | 25° C., 60% RH | >50,000 |
| Comparative Example 12 | Comparative ionic liquid 4 | 25° C., 60% RH | 23,500 |
| Comparative Example 13 | Comparative ionic liquid 5 | 25° C., 60% RH | 11,000 |

As can be seen from Table 6, Examples 18 to 22 in which ionic liquids formed from Bronsted bases containing a hydrocarbon having at least 10 or more carbon atoms were used in magnetic disks had the CSS durability of greater than 50,000 times, indicating that they have superior durabilities to Comparative Examples 12 and 13 in which ionic liquids formed from Bronsted bases containing a hydrocarbon having 8 or less carbon atoms were used.

Next, Examples in which Ionic liquids 5 to 9 and Comparative ionic liquids 4 and 5 were applied to magnetic tapes will now be described.

Example 23

A magnetic tape was produced as described above using the lubricating agent containing Ionic liquid 5. As described in Table 7, the coefficients of friction of the magnetic tapes after 100 times of shuttle runs were 0.22 under the environment of a temperature of −5° C. and 0.23 under the environment of a temperature of 40° C. and a relative humidity of 90%. The still durabilities were 53 min under the environment of a temperature of −5° C. and longer than 60 min under the environment of a temperature of 40° C. and a relative humidity of 30%. The shuttle durabilities were 153 times under the environment of a temperature of −5° C. and 126 times under the environment of a temperature of 40° C. and a relative humidity of 90%. From these results, it has been found that the magnetic tape onto which Ionic liquid 5 was applied has excellent frictional property, still durability, and shuttle durability.

Example 24

A magnetic tape was produced as described above using the lubricating agent containing Ionic liquid 6. As described in Table 7, the coefficients of friction of the magnetic tapes after 100 times of shuttle runs were 0.20 under the environment of a temperature of −5° C. and 0.21 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. From these results, it has been found that the magnetic tape onto which Ionic liquid 6 was applied has excellent frictional property, still durability, and shuttle durability.

Example 25

A magnetic tape was produced as described above using the lubricating agent containing Ionic liquid 7. As described in Table 7, the coefficients of friction of the magnetic tapes after 100 times of shuttle runs were 0.21 under the environment of a temperature of −5° C. and 0.21 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. From these results, it has been found that the magnetic tape onto which Ionic liquid 7 was applied has excellent frictional property, still durability, and shuttle durability.

Example 26

A magnetic tape was produced as described above using the lubricating agent containing Ionic liquid 8. As described in Table 7, the coefficients of friction of the magnetic tapes after 100 times of shuttle runs were 0.22 under the environment of a temperature of −5° C. and 0.22 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. From these results, it has been found that the magnetic tape onto which Ionic liquid 8 was applied has excellent frictional property, still durability, and shuttle durability.

Example 27

A magnetic tape was produced as described above using the lubricating agent containing Ionic liquid 9. As described in Table 7, the coefficients of friction of the magnetic tapes after 100 times of shuttle runs were 0.24 under the environment of a temperature of −5° C. and 0.25 under the environment of a temperature of 40° C. and a relative humidity of 90%. The still durabilities were 51 min under the environment of a temperature of −5° C. and 59 min under the environment of a temperature of 40° C. and a relative humidity of 30%. The shuttle durabilities were 135 times under the environment of a temperature of −5° C. and 158 times under the environment of a temperature of 40° C. and a relative humidity of 90%. From these results, it has been found that the magnetic tape onto which Ionic liquid 9 was applied has excellent frictional property, still durability, and shuttle durability.

Comparative Example 14

A magnetic tape was produced as described above using the lubricating agent containing Comparative ionic liquid 4. As described in Table 7, the coefficients of friction of the magnetic tapes after 100 times of shuttle runs were 0.29 under the environment of a temperature of −5° C. and 0.30 under the environment of a temperature of 40° C. and a relative humidity of 90%. The still durabilities were 35 min under the environment of a temperature of −5° C. and 39 min under the environment of a temperature of 40° C. and a relative humidity of 30%. The shuttle durabilities were 96 times under the environment of a temperature of −5° C. and 95 times under the environment of a temperature of 40° C. and a relative humidity of 90%.

Comparative Example 15

A magnetic tape was produced as described above using the lubricating agent containing Comparative ionic liquid 5. As described in Table 7, the coefficients of friction of the magnetic tapes after 100 times of shuttle runs were 0.36 under the environment of a temperature of −5° C. and 0.41 under the environment of a temperature of 40° C. and a relative humidity of 90%. The still durabilities were 15 min under the environment of a temperature of −5° C. and 25 min under the environment of a temperature of 40° C. and a relative humidity of 30%. The shuttle durabilities were 86 times under the environment of a temperature of −5° C. and 54 times under the environment of a temperature of 40° C. and a relative humidity of 90%.

TABLE 7

| | Lubricating agent | Coefficient of friction after 100 times of shuttle runs | | Still durability/min | | Shuttle durability | |
|---|---|---|---|---|---|---|---|
| Ex. 23 | Ionic liquid 5 | −5° C. | 0.22 | −5° C. | 53 | −5° C. | 153 |
| | | 40° C., 90% RH | 0.23 | 40° C., 30% RH | >60 | 40° C., 90% RH | 126 |
| Ex. 24 | Ionic liquid 6 | −5° C. | 0.20 | −5° C. | >60 | −5° C. | >200 |
| | | 40° C., 90% RH | 0.21 | 40° C., 30% RH | >60 | 40° C., 90% RH | >200 |
| Ex. 25 | Ionic liquid 7 | −5° C. | 0.21 | −5° C. | >60 | −5° C. | >200 |
| | | 40° C., 90% RH | 0.21 | 40° C., 30% RH | >60 | 40° C., 90% RH | >200 |
| Ex. 26 | Ionic liquid 8 | −5° C. | 0.22 | −5° C. | >60 | −5° C. | >200 |
| | | 40° C., 90% RH | 0.22 | 40° C., 30% RH | >60 | 40° C., 90% RH | >200 |
| Ex. 27 | Ionic liquid 9 | −5° C. | 0.24 | −5° C. | 51 | −5° C. | 135 |
| | | 40° C., 90% RH | 0.25 | 40° C., 30% RH | 59 | 40° C., 90% RH | 158 |
| Comp. Ex. 14 | Comparative ionic liquid 4 | −5° C. | 0.29 | −5° C. | 35 | −5° C. | 96 |
| | | 40° C., 90% RH | 0.30 | 40° C., 30% RH | 39 | 40° C., 90% RH | 95 |
| Comp. Ex. 15 | Comparative ionic liquid 5 | −5° C. | 0.36 | −5° C. | 15 | −5° C. | 86 |
| | | 40° C., 90% RH | 0.41 | 40° C., 30% RH | 25 | 40° C., 90% RH | 54 |

As can be seen from Table 7, Examples 23 to 27 in which ionic liquids formed from Bronsted bases containing a hydrocarbon having at least 10 or more carbon atoms were used in magnetic tapes has greatly improved coefficient of friction, still durability, and shuttle durability as compared to Comparative Examples 14 and 15 in which ionic liquids formed from Bronsted bases containing a hydrocarbon having 8 or less carbon atoms were used. Example 26 in which the ionic liquid containing a linear hydrocarbon group having a double bound was used in the magnetic tape and Example 27 in which the ionic liquid having a branched hydrocarbon group was used in the magnetic tape had slightly higher coefficients of friction than those having 14 or more carbon atoms, but had the still durability and the shuttle durability sufficiently satisfying practical specification.

<3.3 Effect of Other Structures than Hydrocarbon Group in Bronsted Base>

Next, ionic liquids were synthesized using, as the Bronsted base, compounds (cyclic amidine) in which other structures than the hydrocarbon group are different from amine. Lubricating agents containing the ionic liquids were used in magnetic recording media to examine an effect of other structures than the hydrocarbon group in the Bronsted base.

Example 28

Synthesis of $C_8F_{17}SO_3^-H_3N^+C_{18}H_{37}$ (Ionic Liquid 10)

Stearylamine was dissolved in a mixed solvent of 85% by mass of n-hexane and 15% by mass of ethanol. An equimolar amount of perfluorooctane sulfonic acid dissolved in ethanol was added thereto, followed by heating at 60° C. for 30 min. After removing the solvent, recrystallization was performed with a mixed solvent of n-hexane and a small amount of ethanol to thereby obtain colorless crystals ($C_8F_{17}SO_3^-H_3N^+C_{18}H_{37}$).

Example 29

Synthesis of 6-pentadecyldiazabicycloundecene (6-pentadecyl-1,8-diazabicyclo[5.4.0]undec-7-ene: 6-pentadecyl DBU)

6-Pentadecyldiazabicycloundecane represented by the following Structural Formula (1) was synthesized according to the paper by Matsumura (N. Matsumura, H. Nishiguchi, M. Okada, and S. Yoneda, J. Heterocyclic Chem. pp. 885-887, Vol/23. Issue 3 (1986)).

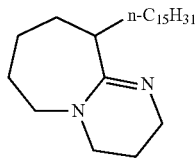

Structural Formula (1)

Synthesis of Ionic Liquid 11

The compound represented by the Structural Formula (1) which had been obtained using the above method was dissolved in a mixed solvent of 85% by mass of n-hexane and 15% by mass of ethanol. Perfluorooctane sulfonic acid dissolved in ethanol was added thereto [95 mol % relative to the compound represented by the Structural Formula (1)]. After removing the solvent, the resultant was washed with n-hexane to remove an excess of compounds represented by the Structural Formula (1) to thereby obtain Ionic liquid 11.

Comparative Example 16

Synthesis of $C_7F_{15}COO^-H_3N^+C_{18}H_{37}$ (Comparative Ionic Liquid 6)

It was synthesized according to Tribology Trans, Vol. 37, No. 1 (January 1994), pp. 99-105.

Comparative Example 17

Synthesis of $C_7F_{15}CH_2O^-H_3N^+C_{18}H_{37}$ (Comparative Ionic Liquid 7)

Stearylamine and an equimolar amount of pentadecafluorooctanol were dissolved in a mixed solvent n-hexane and a small amount of ethanol, followed by heating at 60° C. for 30 min. The resultant was filtered to remove contaminants, followed by recrystallization to thereby obtain colorless crystals.

Table 8 shows the pKa values of the Bronsted acids, the pKa values of the Bronsted base, and ΔpKa values in ionic liquids obtained in Examples 28 and 29 and Comparative Examples 16 and 17.

TABLE 8

|  | Structural Formula of Bronsted acid | Bronsted base | pKa of Bronsted acid | pKa of Bronsted base | ΔpKa |
|---|---|---|---|---|---|
| Example 28 | $C_8F_{17}SO_3H$ | Stearylamine | −3.3 | 10.7 | 14 |
| Example 29 | $C_8F_{17}SO_3H$ | 6-pentadecyl DBU | −3.3 | 12.5 | 15.8 |
| Comparative Example 16 | $C_7F_{15}COOH$ | Stearylamine | 3.8 | 10.7 | 6.9 |
| Comparative Example 17 | $C_7F_{15}CH_2OH$ | Stearylamine | 7-9 | 10.7 | 1.7-3.7 |

<Result of Thermal Analysis>

Figure 4:
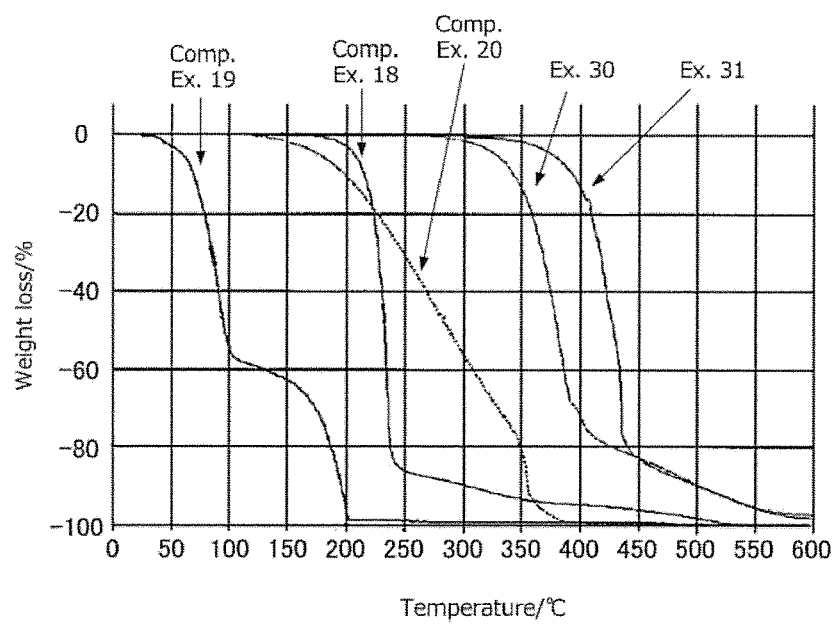
FIG. 4 is a graph showing TG measurement results in Examples.

Ionic liquids obtained from Examples 2, 28, and 29 and Comparative Examples 16 and 17 were subjected to a TG measurement using EXSTAR 6000 (Seiko Instruments Inc.) (Examples 30 and 31, and Comparative Examples 18 and 19). Z-DOL was also subjected to the TG measurement (Comparative Example 20). Weight loss was measured while purging air in a temperature range of 30° C. to 600° C. at a heating rate of 10° C./min. Results are shown in FIG. 4. Also, 10% weight loss temperatures are summarized in Table 9.

Note that, exothermic peak temperatures in a differential thermal analysis (DTA) measurement of Ionic liquid 2 were 374° C. and 380° C., and exothermic peak temperatures in the differential thermal analysis (DTA) measurement of Ionic liquid 10 were 383° C. and 402° C.

TABLE 9

|  | Lubricating agent | 10% weight loss temperature/° C. |
|---|---|---|
| Example 30 | Ionic liquid 10 | 327 |
| Example 31 | Ionic liquid 11 | 372 |
| Comparative Example 18 | Comparative ionic liquid 6 | 205 |
| Comparative Example 19 | Comparative ionic liquid 7 | 62 |
| Comparative Example 20 | Z-DOL | 165 |

From these results, it has been found that Ionic liquids 10 and 11 having the ΔpKa of much greater than 7 have very high 10% weight loss temperatures. In particular, the latter has been found to have the 10% weight loss temperature 200° C. or more higher than that of Z-DOL. In Ionic liquid 11, a DBU derivative having high basic strength was used as the Bronsted base instead of stearylamine, so that the ΔpKa was increased and the 10% weight loss temperature was increased by 45° C. In contrast, Comparative ionic liquid 6 having the ΔpKa of 6.9 had the 10% weight loss temperature of 205° C., and Comparative ionic liquid 7 having the ΔpKa of 4 or less had the 10% weight loss temperature of 62° C., indicating poor thermal resistance.

having the ΔpKa of 12 or more onto a carbon protecting layer formed on the surface of the metal magnetic thin film, have excellent CSS property and improved durability, and these properties are maintained even after the heating. When the ΔpKa is less than 10, the durability after the heating is deteriorated. It is believed that this is because ionic dissociation and decomposition proceed at the high temperature to thereby deteriorate thermal stability.

Examples 32 and 33, and Comparative Examples 21 to 23

Next, Examples applied to metallic thin film type magnetic recording media (magnetic disks) will now be described.

Magnetic disks were produced as described above using lubricating agents containing ionic liquids described in Table 10. The thus produced magnetic disks were subjected to the CSS durability test and the CSS durability test after the heating. Results are shown in Table 10.

Examples 34 and 35, Comparative Examples 24 to 26

Next, Examples applied to magnetic tapes will now be described.

Magnetic tapes were produced as described above using the lubricating agents containing ionic liquids described in

TABLE 10

|  | Lubricating agent | CSS durability | | CSS durability after heating test | |
|---|---|---|---|---|---|
| Example 32 | Ionic liquid 10 | 25° C., 60% RH | >50,000 | 25° C., 60% RH | >50,000 |
| Example 33 | Ionic liquid 11 | 25° C., 60% RH | >50,000 | 25° C., 60% RH | >50,000 |
| Comparative Example 21 | Comparative ionic liquid 6 | 25° C., 60% RH | >50,000 | 25° C., 60% RH | 891 |
| Comparative Example 22 | Comparative ionic liquid 7 | 25° C., 60% RH | >50,000 | 25° C., 60% RH | 156 |
| Comparative Example 23 | Z-DOL | 25° C., 60% RH | >50,000 | 25° C., 60% RH | 12,000 |

As can be seen from Table 10, in Examples 32 and 33, each sample disks, which were produced by applying the ionic liquid, serving as the lubricating agent, formed from the Bronsted acid and the Bronsted base containing a linear hydrocarbon group having 10 or more carbon atoms and Table 11. The thus produced magnetic tapes were examined for the coefficient of friction after 100 times of shuttle runs, the still durability, the shuttle durability, the still durability after the heating, and the shuttle durability after the heating. Results are shown in Table 11.

TABLE 11

|  | Lubricating agent | Coefficient of friction after 100 times of shuttle runs | | Still durability/min | | Shuttle durability/ times | | Still durability after heating/min | | Shuttle durability after heating/times | |
|---|---|---|---|---|---|---|---|---|---|---|---|
| Ex. 34 | Ionic liquid 10 | −5° C. | 0.19 | −5° C. | >60 | −5° C. | >200 | −5° C. | >60 | −5° C. | >200 |
| | | 40° C., 90% RH | 0.23 | 40° C., 30% RH | >60 | 40° C., 90% RH | >200 | 40° C., 30% RH | >60 | 40° C., 90% RH | >200 |
| Ex. 35 | Ionic liquid 11 | −5° C. | 0.2 | −5° C. | >60 | −5° C. | >200 | −5° C. | >60 | −5° C. | >200 |
| | | 40° C., 90% RH | 0.23 | 40° C., 30% RH | >60 | 40° C., 90% RH | >200 | 40° C., 30% RH | >60 | 40° C., 90% RH | >200 |
| Comp. Ex. 24 | Comparative ionic liquid 6 | −5° C. | 0.22 | −5° C. | >60 | −5° C. | >200 | −5° C. | 45 | −5° C. | 130 |
| | | 40° C., 90% RH | 0.25 | 40° C., 30% RH | >60 | 40° C., 90% RH | >200 | 40° C., 30% RH | 36 | 40° C., 90% RH | 123 |
| Comp. Ex. 25 | Comparative ionic liquid 7 | −5° C. | 0.23 | −5° C. | >60 | −5° C. | >200 | −5° C. | 12 | −5° C. | 30 |
| | | 40° C., 90% RH | 0.26 | 40° C., 30% RH | >60 | 40° C., 90% RH | >200 | 40° C., 30% RH | 16 | 40° C., 90% RH | 23 |
| Comp. Ex. 26 | Z-DOL | −5° C. | 0.28 | −5° C. | 12 | −5° C. | 59 | −5° C. | 12 | −5° C. | 46 |
| | | 40° C., 90% RH | 0.3 | 40° C., 30% RH | 48 | 40° C., 90% RH | 124 | 40° C., 30% RH | 15 | 40° C., 90% RH | 58 |

In these results, the magnetic tape onto which the ionic liquid formed from the Bronsted acid and the Bronsted base containing a linear hydrocarbon group having 10 or more carbon atoms, and having the ΔpKa of 12 or more was applied as the lubricating agent showed excellent wear resistance, still durability, and shuttle durability. However, those having the ΔpKa of 7 or less, which were presented as Comparative Examples, were greatly deteriorated in durability as with the aforementioned disks.

Example 36

[Ionic Liquid 12]

Synthesis of n-octadecylamine-bistrifluoromethane sulfonylimide salt

The synthetic scheme is shown below.

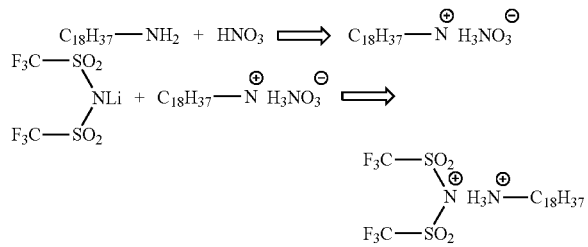

Synthesis of n-octadecylamine-bisnonafluorobutane sulfonylimide salt was performed with reference to the paper by Huang et al. (Non-patent literature: ing-Fang Huang, Huimin Luo, Chengdu Liang, I-Wen Sun, Gary A. Baker, and Sheng Dai, "Hydrophobic Bronsted Acid-Base Ionic Liquids Based on PAMAM Dendrimers with High Proton Conductivity and Blue Photoluminescence," J. Am. Chem. Soc. Vol. 127, 12784-12785 (2005)).

Firstly, 15.18 g of n-octadecylamine was dissolved in ethanol, and 60% concentrated nitric acid (d=1.360) was added dropwise thereto while stirring. When reaching the point of neutralization, the addition was terminated. After cooling, precipitated crystals were filtered, followed by drying to thereby obtain n-octadecylamine nitrate.

Figure 5:
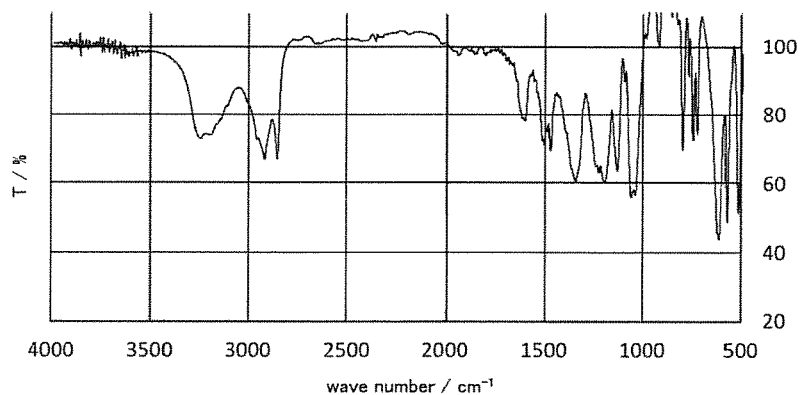
FIG. 5 shows a FTIR spectrum of the product of Example 36.
Figure 6:
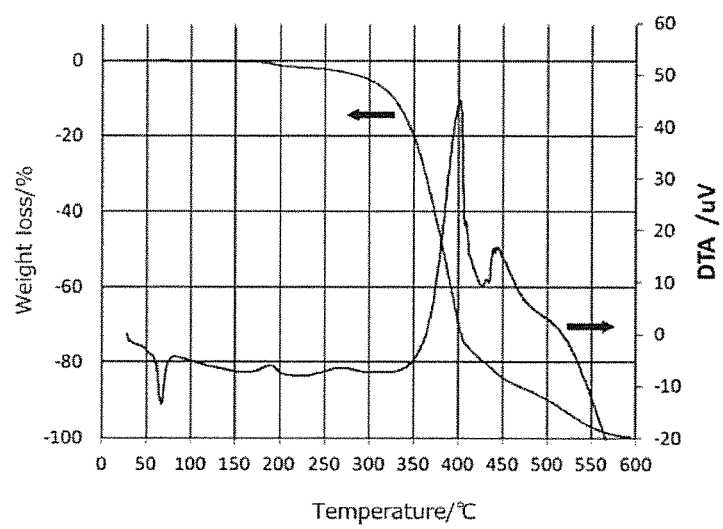
FIG. 6 shows a TG/DTA measurement result of the product of Example 36.

Next, 6.80 g of n-octadecylamine nitrate was dissolved in ethanol, and 5.91 g of bistrifluoromethane sulfoimide lithium salt dissolved in ethanol was added dropwise thereto. After the completion of titration, the resultant was stirred for 1 hour and heated under reflux for 1 hour. The resultant was cooled, followed by removing the solvent therefrom, adding water and diethyl ether thereto, separating an organic layer, and washing the organic layer with water. The organic layer was dried over anhydrous magnesium sulfate, followed by removing the solvent therefrom, and recrystallizing from n-hexane to thereby obtain n-octadecylamine-bistrifluoromethanesulfonylimide salt (colorless crystals, melting point: 67° C.). FTIR spectra and TG/DTA thereof are shown in FIGS. 5 and 6.

In this Example, the FTIR measurement was performed by a transmission method (e.g., a KBr plate method or a KBr tablet method) using FT/IR-460 (manufactured by JASCO Corporation). Resolution was set to 4 cm$^{-1}$.

The TG/DTA measurement was performed in a temperature range of 30° C. to 600° C. at a heating rate of 10° C./min while introducing air at a flow rate of 200 mL/min using EXSTAR 6000 (manufactured by Seiko Instruments Inc.).

As a gas chromatography mass spectrometer, 6890/5975 MSD (manufactured by Agilent Technologies, Inc.) was used. The following measurement conditions were used: column: DB-1 (15 m, diameter: 0.25 mm, membrane thickness: 0.1 μm); injection temperature: 280° C.; column temperature: initial temperature of 40° C., hold for 5 min, heated to 340° C. at the heating rate of 20° C./min, and hold at the same temperature; mass spectrometric unit: 5975MSD; MS detection mode: EI$^+$; quadrupole temperature: 150° C.; ion source temperature: 300° C.; mass scanning range: m/z 33-700; and calibration: PFTBA.

IR absorption wavenumbers and attributes thereof are shown in Table 12. The symmetric stretching vibration of S—N—S bond was observed at 1,038 cm$^{-1}$, the symmetric stretching vibration of SO$_2$ bond was observed at 1,131 cm$^{-1}$, the symmetric stretching vibration of CF$_3$ was observed at 1,194 cm$^{-1}$, the anti-symmetric stretching vibration of SO$_2$ bond was observed at 1,344 cm$^{-1}$, the anti-symmetric deformation vibration of NH$_4^+$ was observed at 1,600 cm$^{-1}$, the symmetric stretching vibration of CH$_2$ was observed at 2,850 cm$^{-1}$, the anti-symmetric stretching vibration of CH$_2$ was observed at 2,916 cm$^{-1}$, and the broad symmetric stretching vibration of NH$_4^+$ was observed at 3,360 cm$^{-1}$ to 3,020 cm$^{-1}$. Based on these results, the structure of the resultant compound was determined.

Additionally, TG/DTA showed that the 10% weight loss temperature was very high of 329° C. and the weight loss was exothermic, suggesting that the weight loss is resulted from decomposition reaction of the compound.

TABLE 12

| Band | Assignment |
|---|---|
| 1,038 cm$^{-1}$ | $v_{as}$*SNS |
| 1,131 cm$^{-1}$ | $v_s$**SO$_2$ |
| 1,194 cm$^{-1}$ | $v_s$CF$_3$ |
| 1,344 cm$^{-1}$ | $v_{as}$SO$_2$ |
| 1,600 cm$^{-1}$ | $\sigma_{as}$***NH$_4^+$ |
| 2,850 cm$^{-1}$ | $v_s$CH$_2$ |
| 2,916 cm$^{-1}$ | $v_{as}$CH$_2$ |
| 3,360 cm$^{-1}$ to 3,020 cm$^{-1}$ | $v_s$NH$_4^+$ |

Example 37

[Ionic Liquid 13]

Synthesis of n-octadecylamine-bisnonafluorobutane sulfonylimide salt

The synthetic scheme is shown below.

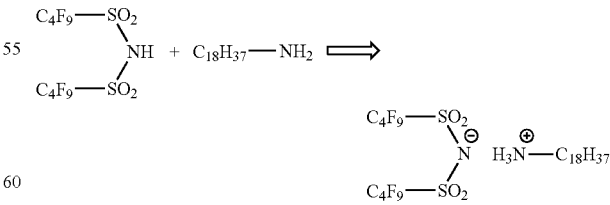

Figure 7:
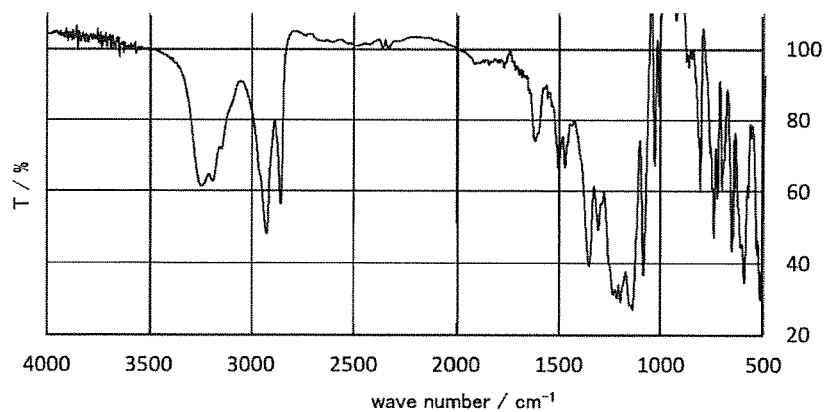
FIG. 7 shows a FTIR spectrum of the product of Example 37.
Figure 8:
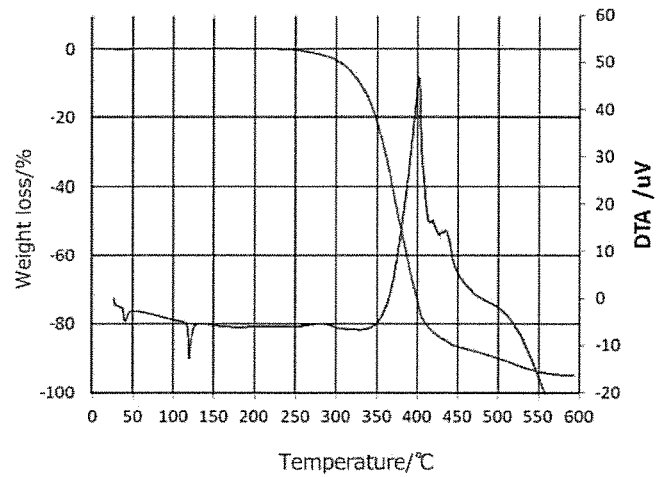
FIG. 8 shows a TG/DTA measurement result of the product of Example 37.

Bisnonafluorobutane sulfonylimide (9.31 g) was dissolved in ethanol, and n-octadecylamine dissolved in ethanol was added thereto. After heating under reflux for 30 min, the solvent was removed. Recrystallization from n-hexane was performed to thereby obtain n-octadecylamine-bisnonafluorobutane sulfonylimide salt (colorless crystals, melting point: 118° C.). FTIR spectra and TG/DTA thereof are shown in FIGS. 7 and 8.

IR absorption wavenumbers and attributes thereof are shown in Table 13. The symmetric stretching vibration of S—N—S bond was observed at 1,031 cm$^{-1}$, the symmetric stretching vibration of SO$_2$ bond was observed at 1,088 cm$^{-1}$, the symmetric stretching vibration of CF$_3$ and CF$_2$ were observed at 1,200 cm$^{-1}$ and 1,141 cm$^{-1}$, the anti-symmetric stretching vibration of SO$_2$ bond was observed at 1,355 cm$^{-1}$, the anti-symmetric deformation vibration of NH$_4^+$ was observed at 1,616 cm$^{-1}$, the symmetric stretching vibration of CH$_2$ was observed at 2,856 cm$^{-1}$, the anti-symmetric stretching vibration of CH$_2$ was observed at 2,926 cm$^{-1}$, and the broad symmetric stretching vibration of NH$_4^+$ was observed at 3,360 cm$^{-1}$ to 3,025 cm$^{-1}$. Based on these results, the structure of the resultant compound was determined.

Additionally, TG/DTA showed that the 10% weight loss temperature was very high of 331° C. and the weight loss was exothermic in this case as well, suggesting that the weight loss is resulted from decomposition reaction of the compound.

TABLE 13

| Band | Assignment |
|---|---|
| 1,031 cm$^{-1}$ | $\nu_{as}$SNS |
| 1,088 cm$^{-1}$ | $\nu_s$SO$_2$ |
| 1,200 cm$^{-1}$, 1,141 cm$^{-1}$ | $\nu_s$CF$_2$, $\nu_s$CF$_3$ |
| 1,355 cm$^{-1}$ | $\nu_a$SO$_2$ |
| 1,616 cm$^{-1}$ | $\sigma_{as}$NH$_4^+$ |
| 2,856 cm$^{-1}$ | $\nu_a$CH$_2$ |
| 2,926 cm$^{-1}$ | $\nu_{as}$CH$_2$ |
| 3,360 cm$^{-1}$ to 3,025 cm$^{-1}$ | $\nu_s$NH$_4^+$ |

Example 38

[Ionic Liquid 14]

Synthesis of n-octadecylamine-cyclo-hexafluoropropane-1,3-bis(sulfonyl)imide salt The synthetic scheme is shown below.

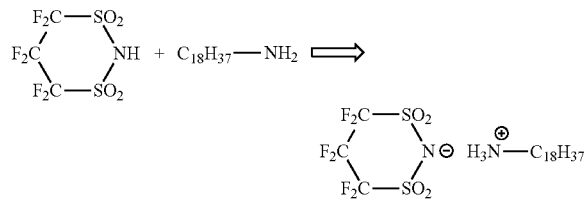

Figure 9:
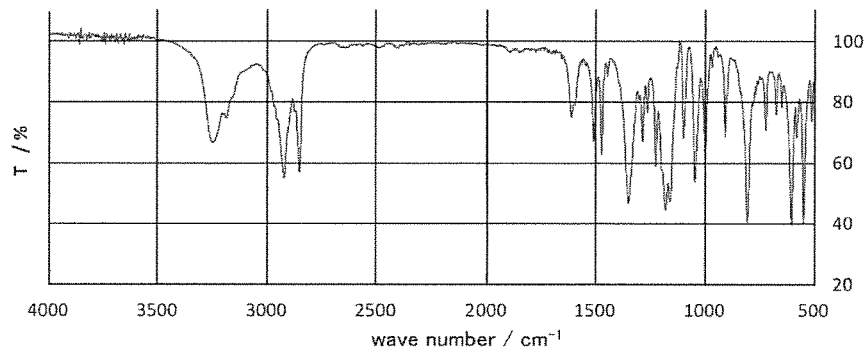
FIG. 9 shows a FTIR spectrum of the product of Example 38.
Figure 10:
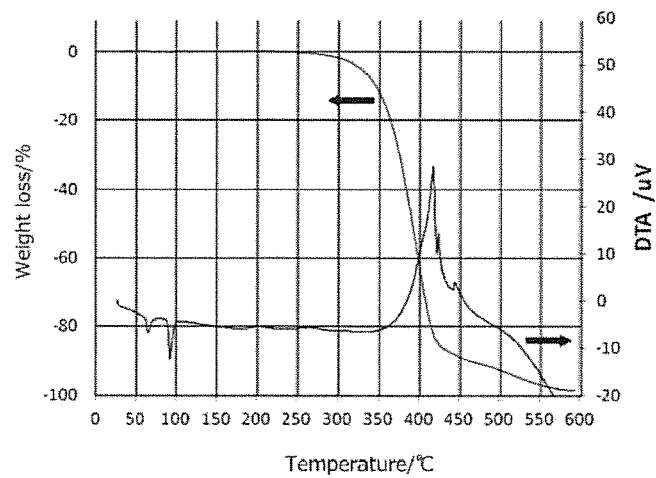
FIG. 10 shows a TG/DTA measurement result of the product of Example 38.

Cyclo-hexafluoropropane-1,3-bis(sulfonyl)imide (5.45 g) was dissolved in ethanol, and n-octadecylamine (5 g) dissolved in ethanol was added thereto. Heat was generated, so that a periphery therearound was cooled with ice. After heating under reflux for 30 min, the solvent was removed. Recrystallization from n-hexane was performed to thereby obtain n-octadecylamine-cyclo-hexafluoropropane-1,3-bis (sulfonyl)imide salt (colorless crystals, melting point: 92° C.). FTIR spectra and TG/DTA thereof are shown in FIGS. 9 and 10.

IR absorption wavenumbers and attributes thereof are shown in Table 14. The symmetric stretching vibration of S—N—S bond was observed at 1,043 cm$^{-1}$, the symmetric stretching vibration of SO$_2$ bond was observed at 1,096 cm$^{-1}$, the symmetric stretching vibration of F$_2$ were observed at 1,188 cm$^{-1}$ and 1,154 cm$^{-1}$, the anti-symmetric stretching vibration of SO$_2$ bond was observed at 1,348 cm$^{-1}$, the anti-symmetric deformation vibration of NH$_4^+$ was observed at 1,608 cm$^{-1}$, the symmetric stretching vibration of CH$_2$ was observed at 2,850 cm$^{-1}$, the anti-symmetric stretching vibration of CH$_2$ was observed at 2,920 cm$^{-1}$, and the broad symmetric stretching vibration of NH$_4^+$ was observed at 3,350 cm$^{-1}$ to 3,035 cm$^{-1}$. Based on these results, the structure of the resultant compound was determined.

Additionally, TG/DTA showed that the 10% weight loss temperature was very high of 347° C. and the weight loss was exothermic in this case as well, suggesting that the weight loss is resulted from decomposition reaction of the compound.

TABLE 14

| Band | Assignment |
|---|---|
| 1,043 cm$^{-1}$ | $\nu_{as}$SNS |
| 1,096 cm$^{-1}$ | $\nu_s$SO$_2$ |
| 1,154 cm$^{-1}$, 1,188 cm$^{-1}$ | $\nu_s$CF$_2$ |
| 1,348 cm$^{-1}$ | $\nu_a$SO$_2$ |
| 1,608 cm$^{-1}$ | $\sigma_{as}$NH$_4^+$ |
| 2,850 cm$^{-1}$ | $\nu_a$CH$_2$ |
| 2,920 cm$^{-1}$ | $\nu_{as}$CH$_2$ |
| 3,350 cm$^{-1}$ to 3,035 cm$^{-1}$ | $\nu_s$NH$_4^+$ |

Example 39

[Ionic Liquid 15]

Synthesis of 6-n-octadecyl-1,8-diazabicyclo[5.4.0]-7-undecene (C18-DBU) pentadecafluorooctane sulfonic acid salt The synthetic scheme of C18-DBU is shown below.

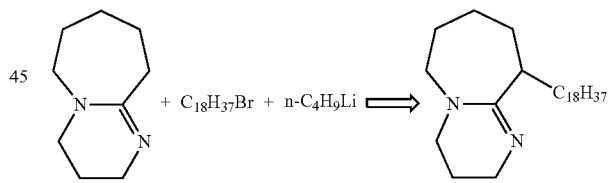

C18-DBU was synthesized with reference to the method by Matsumura et al. (Non-patent literature: Noboru Matsumura, Hiroshi Nishiguchi, Masao Okada, and Shigeo Yoneda, "Preparation and Characterization of 6-Substituted 1,8-diazabicyclo[5.4.0]undec-7-ene," J. Heterocyclic Chemistry Vol. 23, Issue 3, pp. 885-887 (1986)).

Firstly, 7.17 g of 1,8-diazabicyclo[5.4.0]-7-undecene (DBU), which was a raw material, was dissolved in a tetrahydrofuran (THF) solution, followed by cooling to 0° C., adding dropwise 29 cc of n-butyl lithium (1.64 mol/L) thereto under an argon gas atmosphere, and stirring at 0° C. for 1 hour. To the resultant solution, was added dropwise 15.71 g of octadecyl bromide dissolved in THF, followed by leaving to stand with stirring for 24 hours. Note that, THF was dried over type 4A molecular sieves, and then purified by distillation, which was used immediately thereafter. Then, the resultant was acidified with hydrochloric acid, followed by removing the solvent and dissolving in hexane. The resultant was purified by column chromatography using aminated silica gel to thereby obtain a colorless crystal product (yield: 90%).

The thus synthesized product was confirmed to be the intended compound C18-DBU by gas chromatography and mass spectrometry.

Note that, the peak at retention time of 17 min in the gas chromatography had the area ratio of 99.5%.

Next, the synthetic scheme of C18-DBU pentadecafluorooctane sulfonic acid salt is shown below.

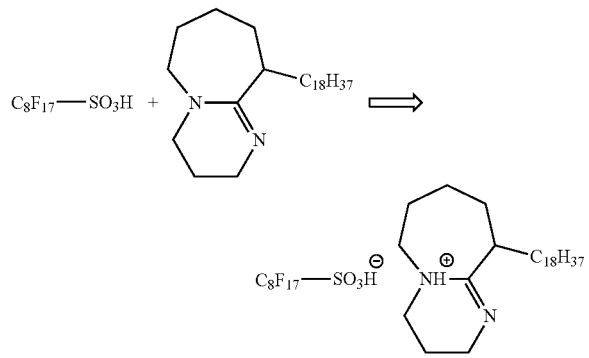

C18-DBU (3.00 g) and heptadecafluorooctane sulfonic acid ($C_8F_{17}SO_3H$) (3.71 g) were dissolved in ethanol with heat, followed by removing the solvent, and recrystallizing from a mixed solvent of n-hexane and ethanol to thereby obtain colorless crystals (melting point: 41° C.).

Figure 11:
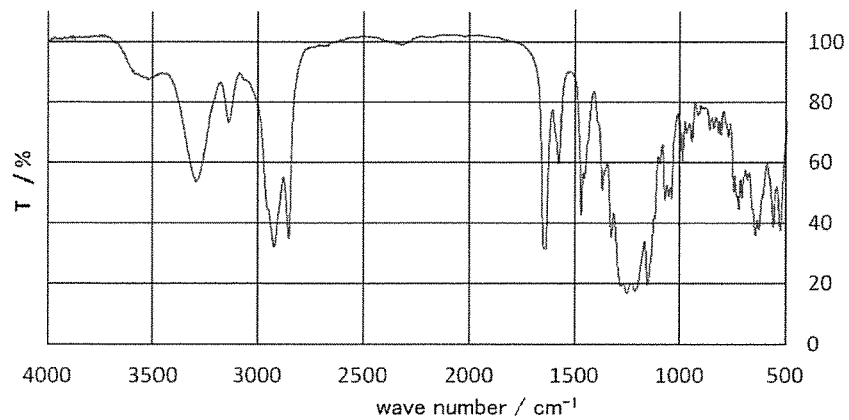
FIG. 11 shows a FTIR spectrum of the product of Example 39.
Figure 12:
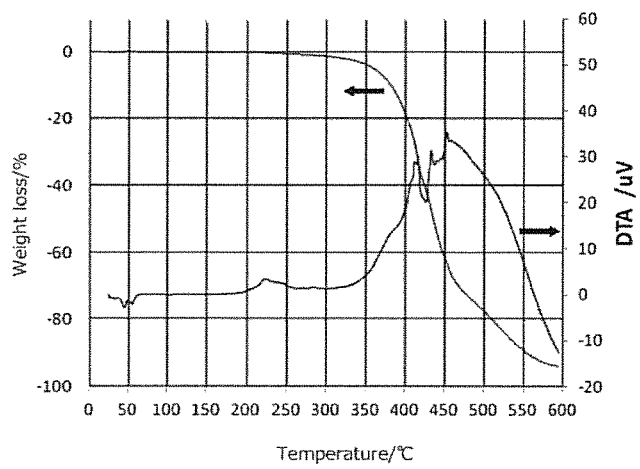
FIG. 12 shows a TG/DTA measurement result of the product of Example 39.

Results of FTIR and TG/DTA are shown in FIGS. 11 and 12.

IR absorption wavenumbers and attributes thereof are shown in Table 15. The symmetric stretching vibration of $CF_3$ and $CF_2$ were observed at 1,252 $cm^{-1}$, the stretching vibration of C=N bond was observed at 1,643 $cm^{-1}$, the symmetric stretching vibration of $CH_2$ was observed at 2,851 $cm^{-1}$, the anti-symmetric stretching vibration of $CH_2$ was observed at 2,920 $cm^{-1}$, and the broad symmetric stretching vibration of $NH^+$ was observed at 3,410 $cm^{-1}$ to 3,178 $cm^{-1}$. Based on these results, the structure of the resultant compound was determined.

Additionally, TG/DTA showed that the 10% weight loss temperature was very high of 384° C. and the weight loss was exothermic in this case as well, suggesting that the weight loss is resulted from decomposition reaction of the compound.

TABLE 15

| Band | Assignment |
|---|---|
| near 1,252 $cm^{-1}$ | $v_sCF_2, v_sCF_3$ |
| 1,643 $cm^{-1}$ | vC=N |
| 2,851 $cm^{-1}$ | $v_aCH_2$ |
| 2,920 $cm^{-1}$ | $v_{as}CH_2$ |
| 3,410 $cm^{-1}$ to 3,178 $cm^{-1}$ | $v_sNH^+$ |

Example 40

[Ionic Liquid 16]

Synthesis of C18-DBU cyclo-hexafluoropropane-1,3-bis(sulfonyl)imide salt

The synthetic scheme of C18-DBU cyclo-hexafluoropropane-1,3-bis(sulfonyl)imide salt is shown below.

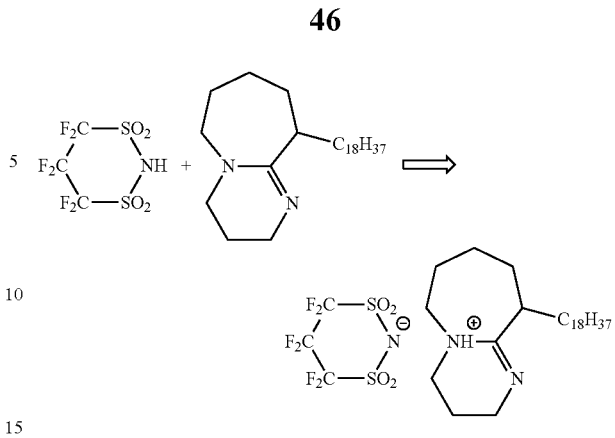

C18-DBU (3.00 g), which was synthesized in the same manner as in Example 39, and cyclo-hexafluoropropane-1,3-bis(sulfonyl)imide (2.18 g) were dissolved in ethanol, followed by heating under reflux for 30 min, removing the solvent, and recrystallizing from n-hexane to thereby obtain colorless crystals (melting point: 52° C.).

Figure 13:
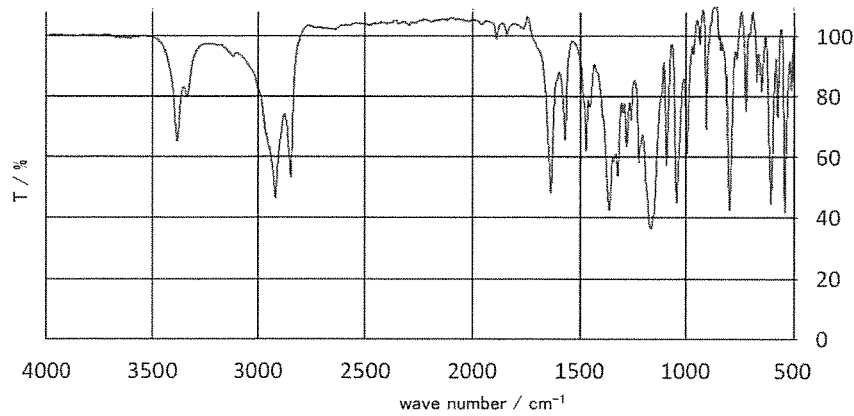
FIG. 13 shows a FTIR spectrum of the product of Example 40.
Figure 14:
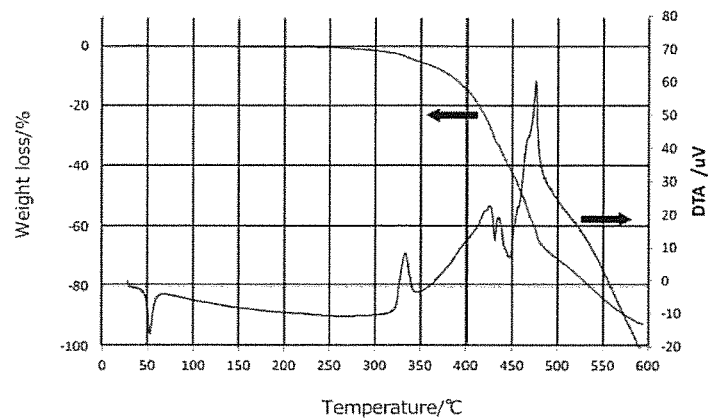
FIG. 14 shows a TG/DTA measurement result of the product of Example 40.

Results of FTIR and TG/DTA are shown in FIGS. 13 and 14.

IR absorption wavenumbers and attributes thereof are shown in Table 16. The symmetric stretching vibration of S—N—S bond was observed at 1,042 $cm^{-1}$, the symmetric stretching vibration of $SO_2$ bond was observed at 1,091 $cm^{-1}$, the symmetric stretching vibration of $CF_2$ was observed at 1,164 $cm^{-1}$, the anti-symmetric stretching vibration of $SO_2$ bond was observed at 1,360 $cm^{-1}$, the stretching vibration of C=N was observed at 1,633 $cm^{-1}$, the symmetric stretching vibration of $CH_2$ was observed at 2,848 $cm^{-1}$, the anti-symmetric stretching vibration of $CH_2$ was observed at 2,920 $cm^{-1}$, and the broad symmetric stretching vibration of $NH^+$ was observed at 3,387 $cm^{-1}$. Based on these results, the structure of the resultant compound was determined.

Additionally, TG/DTA showed that the 10% weight loss temperature was very high of 386° C. and the weight loss was exothermic in this case as well, suggesting that the weight loss is resulted from decomposition reaction of the compound.

TABLE 16

| Band | Assignment |
|---|---|
| 1,042 $cm^{-1}$ | $v_aSNS$ |
| 1,091 $cm^{-1}$ | $v_sSO_2$ |
| 1,164 $cm^{-1}$ | $v_sCF_2$ |
| 1,360 $cm^{-1}$ | $v_aSO_2$ |
| 1,633 $cm^{-1}$ | vC=N |
| 2,848 $cm^{-1}$ | $v_aCH_2$ |
| 2,920 $cm^{-1}$ | $v_{as}CH_2$ |
| 3,387 $cm^{-1}$ | $v_sNH^+$ |

Example 41

[Ionic Liquid 17]

Synthesis of 7-n-octadecyl-1,5,7-triazabicyclo[4.4.0]-5-decene (C18-TBD) pentadecafluorooctane sulfonic acid salt Firstly, the synthetic scheme of 7-n-octadecyl-1,5,7-triazabicyclo[4.4.0]-5-decene (C18-TBD), which is a raw material, is shown below.

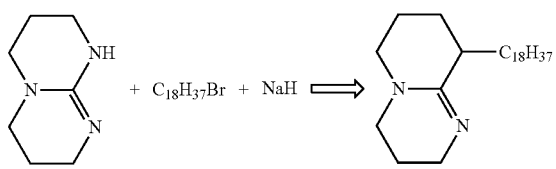

It was synthesized with reference to the method by R. W. Alder et al. (Non-patent literature: Roger W. Alder, Rodney W. Mowlam, David J. Vachon and Gray R. Weisman, "New Synthetic Routes to Macrocyclic Triamines," J. Chem. Sos. Chem. Commun. pp. 507-508 (1992)).

That is, sodium hydride (55% by mass hexane) was added at 10° C. to 8.72 g of 1,5,7-triazabicyclo[4.4.0]-5-decene (TBD), which was produced in the same manner as in Example 39, dissolved in dry THF, followed by stirring. While maintaining the temperature at 10° C., octadecane bromide was added dropwise thereto for 20 min, followed by stirring for 30 min at that temperature and 2 hour at room temperature, and heating under reflux for 1 hour. The resultant was cooled to room temperature, and then an excess of sodium hydride was allowed to react with the addition of ethanol. The solvent was removed therefrom and the resultant was subjected to column chromatography using aminated silica gel to thereby obtain the intended light yellow product.

The thus synthesized product was confirmed to be the intended compound C18-TBD (molecular weight: 391) by gas chromatography and mass spectrometry.

Note that, in the gas chromatography, impurities from the solvent was observed at 10.5 min, but the peak at retention time of 17 min had the area ratio of 98%.

Next, the synthetic scheme of C18-TBD pentadecafluorooctane sulfonic acid salt is shown below.

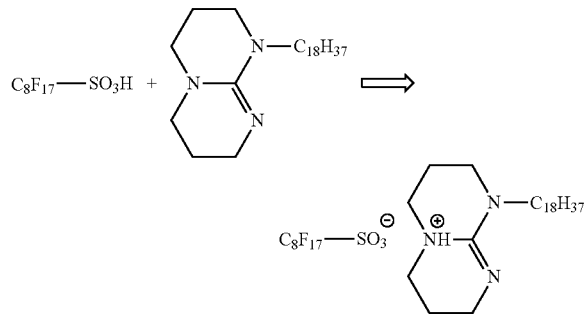

C18-TBD (3.91 g) and pentadecafluorooctane sulfonic acid (5.00 g) were dissolved in ethanol, followed by heating under reflux for 30 min, removing the solvent therefrom, and recrystallizing from n-hexane to thereby obtain colorless crystals (melting point: 65° C.).

Figure 15:
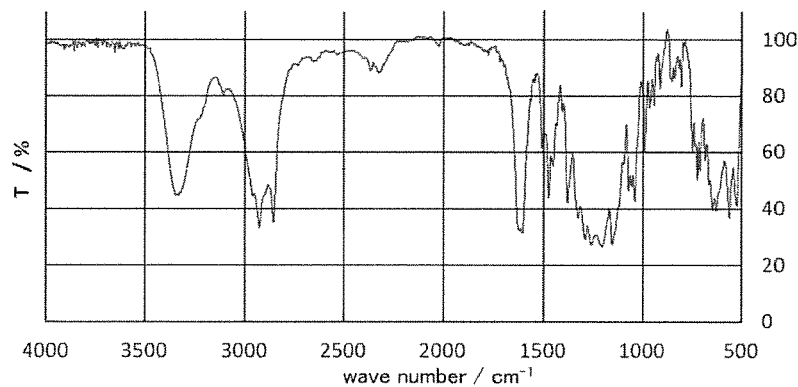
FIG. 15 shows a FTIR spectrum of the product of Example 41.
Figure 16:
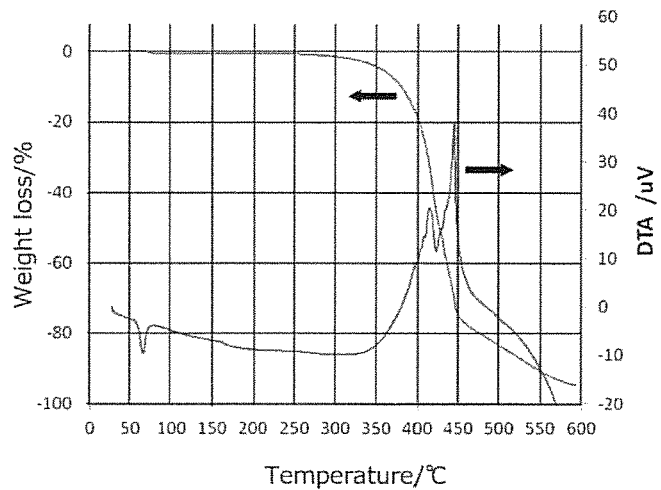
FIG. 16 shows a TG/DTA measurement result of the product of Example 41.

IR and TG/DTA are shown in FIGS. 15 and 16.

IR absorption wavenumbers and attributes thereof are shown in Table 17. The symmetric stretching vibration of $CF_3$ and $CF_2$ was observed at near 1,255 $cm^{-1}$, the stretching vibration of C=N was observed at 1,602 $cm^{-1}$, the symmetric stretching vibration of $CH_2$ was observed at 2,851 $cm^{-1}$, the anti-symmetric stretching vibration of $CH_2$ was observed at 2,924 $cm^{-1}$, and the symmetric stretching vibration of $NH^+$ was observed at 3,289 $cm^{-1}$. Based on these results, the structure of the resultant compound was determined.

Additionally, TG/DTA showed that the 10% weight loss temperature was very high of 381° C. and the weight loss was exothermic in this case as well, suggesting that the weight loss is resulted from decomposition reaction of the compound.

TABLE 17

| Band | Assignment |
| --- | --- |
| near 1,255 $cm^{-1}$ | $v_sCF_2$ |
| 1,602 $cm^{-1}$ | $vC{=}N$ |
| 2,851 $cm^{-1}$ | $v_aCH_2$ |
| 2,924 $cm^{-1}$ | $v_{as}CH_2$ |
| 3,289 $cm^{-1}$ (broad) | $v_sNH^+$ |

Example 42

[Ionic Liquid 18]

Synthesis of C18-TBD cyclo-hexafluoropropane-1,3-bis(sulfonyl)imide salt

The synthetic scheme of C18-TBD cyclo-hexafluoropropane-1,3-bis(sulfonyl)imide salt is shown below.

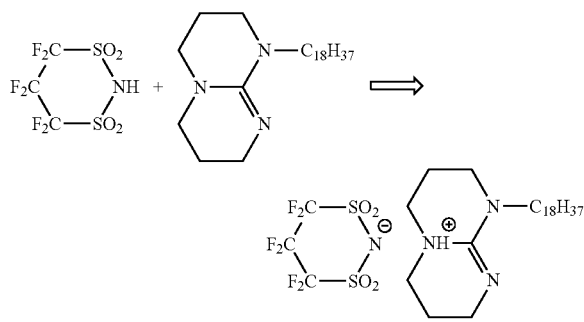

C18-TBD (4.00 g), which was synthesized in the same manner as in Example 41, and hexafluoropropanesulfonylimide (3.00 g) were dissolved in ethanol, followed by heating under reflux for 30 min, removing the solvent therefrom, and recrystallizing from a mixed solvent of n-hexane and ethanol to thereby obtain colorless crystals (melting point: 67° C.).

Figure 17:
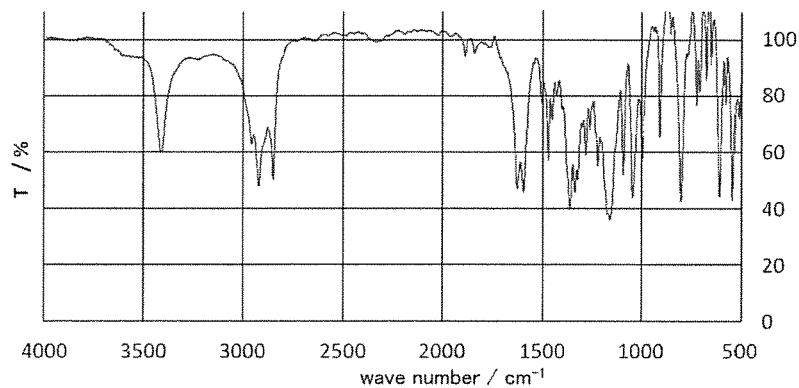
FIG. 17 shows a FTIR spectrum of the product of Example 42.
Figure 18:
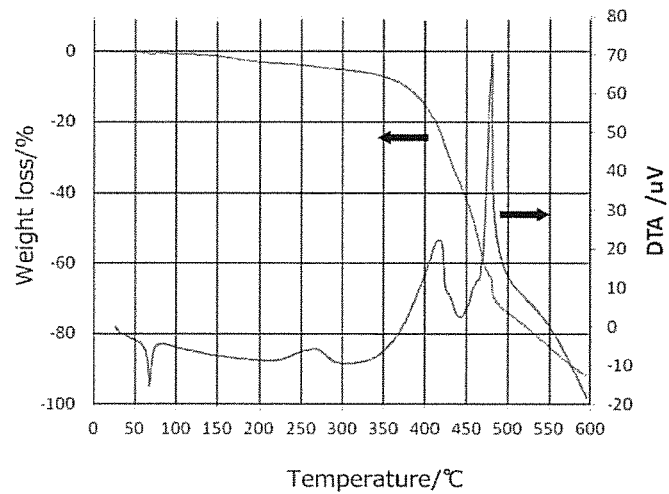
FIG. 18 shows a TG/DTA measurement result of the product of Example 42.

Results of FTIR and TG/DTA are shown in FIGS. 17 and 18.

IR absorption wavenumbers and attributes thereof are shown in Table 18. The symmetric stretching vibration of S—N—S bond was observed at 1,042 $cm^{-1}$, the symmetric stretching vibration of $SO_2$ bond was observed at 1,092 $cm^{-1}$, the symmetric stretching vibration of $CF_2$ was observed at 1,157 $cm^{-1}$, the anti-symmetric stretching vibration of $SO_2$ bond was observed at 1,361 $cm^{-1}$, the stretching vibration of C=N was observed at 1,628 $cm^{-1}$, the symmetric stretching vibration of $CH_2$ was observed at 2,849 $cm^{-1}$, the anti-symmetric stretching vibration of $CH_2$ was observed at 2,921 $cm^{-1}$, and the symmetric stretching vibration of $NH^+$ was observed at 3,412 $cm^{-1}$. Based on these results, the structure of the resultant compound was determined.

Additionally, TG/DTA showed that the 10% weight loss temperature was very high of 380° C. and the weight loss was exothermic in this case as well, suggesting that the weight loss is resulted from decomposition reaction of the compound.

TABLE 18

| Band | Assignment |
|---|---|
| 1,042 cm$^{-1}$ | $v_a$SNS |
| 1,092 cm$^{-1}$ | $v_s$SO$_2$ |
| 1,157 cm$^{-1}$ | $v_s$CF$_2$ |
| 1,361 cm$^{-1}$ | $v_a$SO$_2$ |
| 1,628 cm$^{-1}$ | vC=N |
| 2,849 cm$^{-1}$ | $v_a$CH$_2$ |
| 2,921 cm$^{-1}$ | $v_{as}$CH$_2$ |
| 3,412 cm$^{-1}$ | $v_s$NH$^+$ |

Comparative Example 27

Comparative Ionic Liquid 8

Synthesis of DBU pentadecafluorooctane sulfonic acid salt

The synthetic scheme of DBU pentadecafluorooctane sulfonic acid salt is shown below.

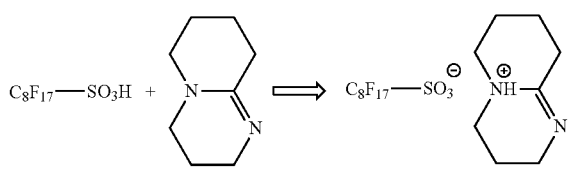

DBU was used as received from Tokyo Chemical Industry Co., Ltd. without further purification. DBU (5.00 g) and pentadecafluorooctane sulfonic acid (1.52 g) were dissolved in ethanol, followed by heating under reflux for 30 min, removing the solvent therefrom, and recrystallizing from a mixed solvent of n-hexane and ethanol to thereby obtain colorless crystals (melting point: 121° C.).

Figure 19:
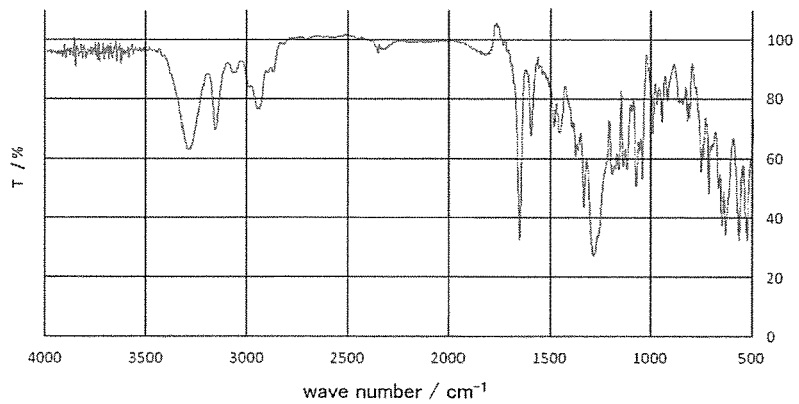
FIG. 19 shows a FTIR spectrum of the product of Comparative Example 27.
Figure 20:
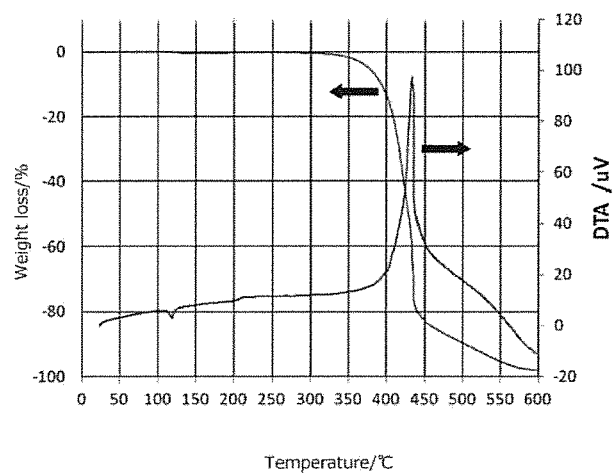
FIG. 20 shows a TG/DTA measurement result of the product of Comparative Example 27.

Results of FTIR and TG/DTA are shown in FIGS. 19 and 20.

IR absorption wavenumbers and attributes thereof are shown in Table 19. The symmetric stretching vibration of CF$_3$ and CF$_2$ was observed at near 1,282 cm$^{-1}$, the stretching vibration of C=N was observed at 1,651 cm$^{-1}$, the symmetric stretching vibration of CH$_2$ was observed at 2,868 cm$^{-1}$, the anti-symmetric stretching vibration of CH$_2$ was observed at 2,943 cm$^{-1}$, and the broad symmetric stretching vibration of NH$^+$ was observed at 3,289 cm$^{-1}$. Based on these results, the structure of the resultant compound was determined.

Additionally, TG/DTA showed that the 10% weight loss temperature was very high of 393° C. and the weight loss was exothermic in this case as well, suggesting that the weight loss is resulted from decomposition reaction of the compound.

TABLE 19

| Band | Assignment |
|---|---|
| 1,282 cm$^{-1}$ | $v_s$CF$_2$ |
| 1,651 cm$^{-1}$ | vC=N |
| 2,868 cm$^{-1}$ | $v_a$CH$_2$ |
| 2,943 cm$^{-1}$ | $v_{as}$CH$_2$ |
| 3,289 cm$^{-1}$ | $v_s$NH$^+$ |

Comparative Example 28

Comparative Ionic Liquid 9

Synthesis of TBD pentadecafluoro sulfonic acid salt

TBD was used as received from Tokyo Chemical Industry Co., Ltd. without further purification. The synthetic scheme of TBD pentadecafluoro sulfonic acid salt is shown below.

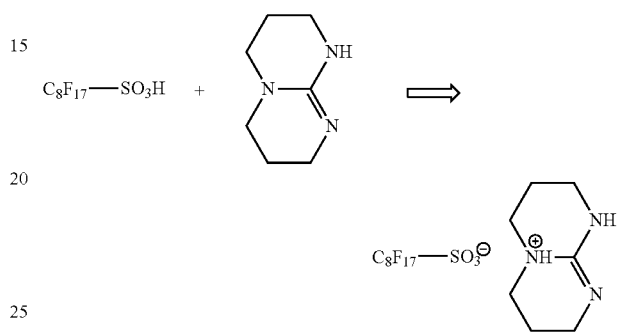

TBU (1.50 g) and pentadecafluorooctane sulfonic acid (5.39 g) were dissolved in ethanol, followed by heating under reflux for 30 min, removing the solvent therefrom, and recrystallizing from n-hexane to thereby obtain colorless crystals (melting point: 84° C.).

Figure 21:
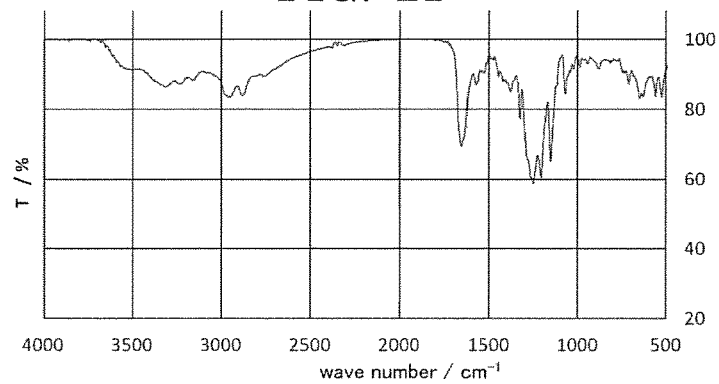
FIG. 21 shows a FTIR spectrum of the product of Comparative Example 28.
Figure 22:
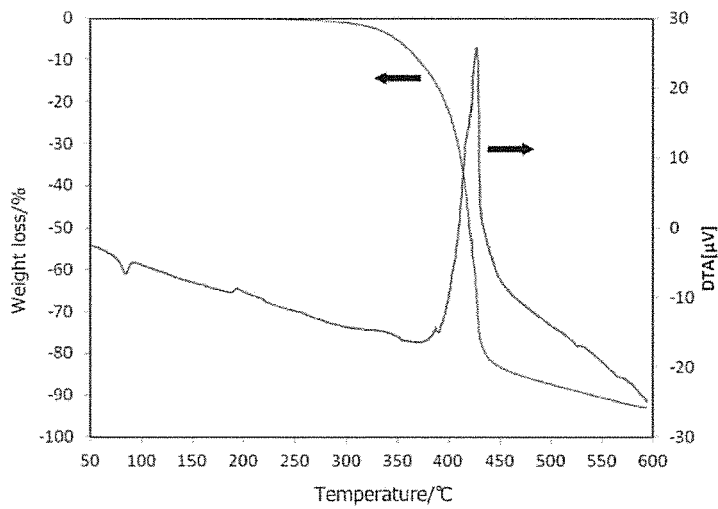
FIG. 22 shows a TG/DTA measurement result of the product of Comparative Example 28.

FTIR and TG/DTA are shown in FIGS. 21 and 22.

IR absorption wavenumbers and attributes thereof are shown in Table 20. The symmetric stretching vibration of CF$_3$ and CF$_2$ was observed at 1,202 cm$^{-1}$ and 1,247 cm$^{-1}$, the stretching vibration of C=N was observed at 1,633 cm$^{-1}$, the symmetric stretching vibration of CH$_2$ was observed at 2,876 cm$^{-1}$, the anti-symmetric stretching vibration of CH$_2$ was observed at 2,933 cm$^{-1}$, and the symmetric stretching vibration of NH$^+$ was observed at 3,040 cm$^{-1}$ to 3,629 cm$^{-1}$. Based on these results, the structure of the resultant compound was determined.

Additionally, TG/DTA showed that the 10% weight loss temperature was very high of 371° C. and the weight loss was exothermic in this case as well, suggesting that the weight loss is resulted from decomposition reaction of the compound.

TABLE 20

| Band | Assignment |
|---|---|
| 1,247 cm$^{-1}$, 1,202 cm$^{-1}$ | $v_s$CF$_3$ and $v_s$CF$_2$ |
| 1,633 cm$^{-1}$ | vC=N |
| 2,876 cm$^{-1}$ | $v_a$CH$_2$ |
| 2,933 cm$^{-1}$ | $v_{as}$CH$_2$ |
| 3,040 cm$^{-1}$ to 3,629 cm$^{-1}$ | $v_s$NH$^+$ |

Synthesized ionic liquids are summarized in the following Table 21.

TABLE 21

| Name | Compound | Exothermic peak temperature in DTA measurement/° C. | 10% weight loss temperature/° C. | Melting point/° C. | ΔpKa |
|---|---|---|---|---|---|
| Ionic liquid 12 (Ex. 36) | n-octadecylamine-bistrifluoromethane sulfonimide salt | 400, 422 | 329 | 67 | 17.9 |
| Ionic liquid 13 (Ex. 37) | n-octadecylamine-bisnonafluorobutane sulfonimide salt | 400, 438 | 331 | 118 | 18.3 |
| Ionic liquid 14 (Ex. 38) | n-octadecylamine-cyclo-hexafluoropropane-1,3-bis(sulfonyl)imide salt | 417 | 347 | 92 | 19.2 |
| Ionic liquid 15 (Ex. 39) | C18-DBU Pentadecafluorooctane sulfonic acid salt | 434, 468 | 384 | 41 | 23.6 |
| Ionic liquid 16 (Ex. 40) | C18-DBU cyclo-hexafluoropropane-1,3-bis(sulfonyl)imide | 474 | 386 | 52 | 25.2 |
| Ionic liquid 17 (Ex. 41) | C18-TBD Pentadecafluorooctane sulfonic acid salt | 412, 444 | 381 | 65 | 24.8 |
| Ionic liquid 18 (Ex. 42) | C18-TBD cyclo-hexafluoropropane-1,3-bis(sulfonyl)imide | 410, 480 | 380 | 67 | 26.4 |
| Comparative ionic liquid 8 (Comp. Ex. 27) | DBU Pentadecafluorooctane sulfonic acid salt | 432 | 393 | 121 | 23.6 |
| Comparative ionic liquid 9 (Comp. Ex. 28) | TBD Pentadecafluorooctane sulfonic acid salt | 425 | 371 | 84 | 24.8 |

The ionic liquids synthesized in Examples 36 to 42 were determined as Ionic liquids 12 to 18. The ionic liquids synthesized in Comparative Examples 27 and 28 were determined as Comparative ionic liquids 8 and 9. The 10% weight loss temperatures thereof are also described.

The ionic liquids synthesized herein including Comparative ionic liquids have a high decomposition temperature and the 10% weight loss temperature of 320° C. or higher because of ΔpKa between the acid and the base of 12 or more.

Example 43

A magnetic disk was produced as described above using a lubricating agent containing n-octadecylamine-bistrifluoromethane sulfonylimide salt which is [Ionic liquid 12]. As described in Table 23, the CSS measurement result of the magnetic disk was greater than 50,000, and the CSS measurement result after the heating test was also greater than 50,000, indicating excellent durability.

Example 44

A magnetic disk was produced as described above using a lubricating agent containing n-octadecylamine-bisnonafluorobutane sulfonylimide salt which is [Ionic liquid 13]. As described in Table 23, the CSS measurement result of the magnetic disk was greater than 50,000, and the CSS measurement result after the heating test was also greater than 50,000, indicating excellent durability.

Example 45

A magnetic disk was produced as described above using a lubricating agent containing n-octadecylamine-cyclo-hexafluoropropane-1,3-bis(sulfonyl)imide salt which is [Ionic liquid 14]. As described in Table 23, the CSS measurement result of the magnetic disk was greater than 50,000, and the CSS measurement result after the heating test was also greater than 50,000, indicating excellent durability.

Example 46

A magnetic disk was produced as described above using a lubricating agent containing C18-DBU pentadecafluorooctane sulfonic acid salt which is [Ionic liquid 15]. As described in Table 23, the CSS measurement result of the magnetic disk was greater than 50,000, and the CSS measurement result after the heating test was also greater than 50,000, indicating excellent durability.

Example 47

A magnetic disk was produced as described above using a lubricating agent containing C18-DBU cyclo-hexafluoropropane-1,3-bis(sulfonyl)imide salt which is [Ionic liquid 16]. As described in Table 23, the CSS measurement result of the magnetic disk was greater than 50,000, and the CSS measurement result after the heating test was also greater than 50,000, indicating excellent durability.

Example 48

A magnetic disk was produced as described above using a lubricating agent containing C18-TBD pentadecafluorooctane sulfonic acid salt which is [Ionic liquid 17]. As described in Table 23, the CSS measurement result of the magnetic disk was greater than 50,000, and the CSS measurement result after the heating test was also greater than 50,000, indicating excellent durability.

Example 49

A magnetic disk was produced as described above using a lubricating agent containing C18-TBD cyclo-hexafluoropropane-1,3-bis(sulfonyl)imide salt which is [Ionic liquid 18]. As described in Table 23, the CSS measurement result of the magnetic disk was greater than 50,000, and the CSS measurement result after the heating test was also greater than 50,000, indicating excellent durability.

Comparative Example 29

A magnetic disk was produced as described above using a lubricating agent containing DBU pentadecafluorooctane sulfonic acid salt which is [Comparative ionic liquid 8]. As described in Table 23, the CSS measurement result of the magnetic disk was 5,860, and the CSS measurement result after the heating test was 14,230. It is believed that the coefficient of friction was increased because the lubricating agent contained no long-chain hydrocarbon.

Comparative Example 30

A magnetic disk was produced as described above using a lubricating agent containing TBD pentadecafluorooctane sulfonic acid salt which is [Comparative ionic liquid 9]. As described in Table 23, the CSS measurement result of the magnetic disk was 6,230, and the CSS measurement result after the heating test was 18,501. It is believed that the coefficient of friction was increased because the lubricating agent contained no long-chain hydrocarbon.

TABLE 23

| | Lubricating agent | CSS durability/ 25° C., 60% RH | CSS durability after heating/25° C., 60% RH |
|---|---|---|---|
| Example 43 | Ionic liquid 12 | >50,000 | >50,000 |
| Example 44 | Ionic liquid 13 | >50,000 | >50,000 |
| Example 45 | Ionic liquid 14 | >50,000 | >50,000 |
| Example 46 | Ionic liquid 15 | >50,000 | >50,000 |
| Example 47 | Ionic liquid 16 | >50,000 | >50,000 |
| Example 48 | Ionic liquid 17 | >50,000 | >50,000 |
| Example 49 | Ionic liquid 18 | >50,000 | >50,000 |
| Comparative Example 29 | Comparative ionic liquid 8 | 5,860 | 14,230 |
| Comparative Example 30 | Comparative ionic liquid 9 | 6,230 | 18,501 |

As clearly can be seen from the above description, the lubricating agent containing the ionic liquid which consists of the Bronsted acid and the Bronsted base containing a linear hydrocarbon group having at least 10 or more carbon atoms and which has the difference of the pKa values thereof (ΔpKa) of 6 or more can maintain an excellent lubricating property even under a high temperature storage condition, and can maintain its CSS lubricating property for a long period of time.

Next, Examples applied to magnetic tapes will now be described.

Example 50

A magnetic tape was produced as described above using the lubricating agent containing Ionic liquid 12. As described in Table 24, the coefficients of friction of the magnetic tapes after 100 times of shuttle runs were 0.19 under the environment of a temperature of −5° C. and 0.23 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 12 was applied has excellent frictional property, still durability, and shuttle durability.

Example 51

A magnetic tape was produced as described above using the lubricating agent containing Ionic liquid 13. As described in Table 24, the coefficients of friction of the magnetic tapes after 100 times of shuttle runs were 0.20 under the environment of a temperature of −5° C. and 0.22 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 13 was applied has excellent frictional property, still durability, and shuttle durability.

Example 52

A magnetic tape was produced as described above using the lubricating agent containing Ionic liquid 14. As described in Table 24, the coefficients of friction of the magnetic tapes after 100 times of shuttle runs were 0.21 under the environment of a temperature of −5° C. and 0.24 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 14 was applied has excellent frictional property, still durability, and shuttle durability.

Example 53

A magnetic tape was produced as described above using the lubricating agent containing Ionic liquid 15. As described in Table 24, the coefficients of friction of the magnetic tapes after 100 times of shuttle runs were 0.22 under the environment of a temperature of −5° C. and 0.26 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 15 was applied has excellent frictional property, still durability, and shuttle durability.

Example 54

A magnetic tape was produced as described above using the lubricating agent containing Ionic liquid 16. As described in Table 24, the coefficients of friction of the magnetic tapes after 100 times of shuttle runs were 0.23 under the environment of a temperature of −5° C. and 0.26 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 16 was applied has excellent frictional property, still durability, and shuttle durability.

Example 55

A magnetic tape was produced as described above using the lubricating agent containing Ionic liquid 17. As described in Table 24, the coefficients of friction of the magnetic tapes after 100 times of shuttle runs were 0.24 under the environment of a temperature of −5° C. and 0.28 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 17 was applied has excellent frictional property, still durability, and shuttle durability.

Example 56

A magnetic tape was produced as described above using the lubricating agent containing Ionic liquid 18. As described in Table 24, the coefficients of friction of the magnetic tapes after 100 times of shuttle runs were 0.23 under the environment of a temperature of −5° C. and 0.27 under the environment of a temperature of 40° C. and a relative humidity of 90%. The still durabilities were longer than 60 min under the environment of a temperature of −5° C. and longer than 60 min under the environment of a temperature of 40° C. and a relative humidity of 30%. The shuttle durabilities were greater than 200 times under the environment of a temperature of −5° C. and greater than 200 times under the environment of a temperature of 40° C. and a relative humidity of 90%. The still durabilities after the heating tests were longer than 60 min under the environment of a temperature of −5° C. and longer than 60 min under the environment of a temperature of 40° C. and a relative humidity of 30%. The shuttle durabilities after the heating tests were greater than 200 times under the environment of a temperature of −5° C. and greater than 200 times under the environment of a temperature of 40° C. and a relative humidity of 90%. From these results, it has been found that the magnetic tape onto which Ionic liquid 18 was applied has excellent frictional property, still durability, and shuttle durability.

Comparative Example 31

A magnetic tape was produced as described above using the lubricating agent containing Comparative ionic liquid 8. As described in Table 24, the coefficients of friction of the magnetic tapes after 100 times of shuttle runs were 0.45 under the environment of a temperature of −5° C. and 0.49 under the environment of a temperature of 40° C. and a relative humidity of 90%. The still durabilities were 18 min under the environment of a temperature of −5° C. and 16 min under the environment of a temperature of 40° C. and a relative humidity of 30%. The shuttle durabilities were 56 times under the environment of a temperature of −5° C. and 45 times under the environment of a temperature of 40° C. and a relative humidity of 90%. The still durabilities after the heating tests were 14 min under the environment of a temperature of −5° C. and 8 min under the environment of a temperature of 40° C. and a relative humidity of 30%. The shuttle durabilities after the heating tests were 36 times under the environment of a temperature of −5° C. and 30 times under the environment of a temperature of 40° C. and a relative humidity of 90%. From these results, it has been found that the magnetic tape onto which Comparative ionic liquid 8 was applied is greatly deteriorated in the still durability after the heating test and the shuttle durability after the heating test.

Comparative Example 32

A magnetic tape was produced as described above using the lubricating agent containing Comparative ionic liquid 9. As described in Table 24, the coefficients of friction of the magnetic tapes after 100 times of shuttle runs were 0.50 under the environment of a temperature of −5° C. and 0.55 under the environment of a temperature of 40° C. and a relative humidity of 90%. The still durabilities were 16 min under the environment of a temperature of −5° C. and 14 min under the environment of a temperature of 40° C. and a relative humidity of 30%. The shuttle durabilities were 45 times under the environment of a temperature of −5° C. and 36 times under the environment of a temperature of 40° C. and a relative humidity of 90%. The still durabilities after the heating tests were 12 min under the environment of a temperature of −5° C. and 10 min under the environment of a temperature of 40° C. and a relative humidity of 30%. The shuttle durabilities after the heating tests were 28 times under the environment of a temperature of −5° C. and 25 times under the environment of a temperature of 40° C. and a relative humidity of 90%. From these results, it has been found that the magnetic tape onto which Comparative ionic liquid 9 was applied is greatly deteriorated in the still durability after the heating test and the shuttle durability after the heating test.

As clearly can be seen from the above description, the lubricating agent containing the ionic liquid which consists of the Bronsted acid and the Bronsted base containing a linear hydrocarbon group having at least 10 or more carbon atoms and which has the difference of the pKa values thereof (ΔpKa) of 12 or more in water or of 6 or more in acetonitrile can maintain the lubricating property even under a high temperature storage condition, and can maintain the lubricating property for a long period of time. Therefore, the magnetic recording medium using the lubricating agent containing the ionic liquid can attain very excellent runnability, wear resistance, and durability.

REFERENCE SIGNS LIST

11 Substrate
12 Under layer
13 Magnetic layer
14 Carbon protecting layer
15 Lubricating agent layer
21 Substrate
22 Magnetic layer
23 Carbon protecting layer
24 Lubricating agent layer
25 Back coat layer

What is claimed is:
1. A magnetic recording medium, comprising:
a non-magnetic support; and
at least a magnetic layer on or above the non-magnetic support,
wherein the magnetic layer contains a lubricating agent comprising:
an ionic liquid formed from a Bronsted acid (HX) and a Bronsted base (B),
wherein the ionic liquid is represented by the following General Formula (1), (2) or (3),
wherein the Bronsted acid is trifluoromethane sulfonic acid, a compound represented by the following Structural Formula (A), a compound represented by the following Structural Formula (B), a compound represented by the following Structural Formula (C), or a compound represented by the following Structural Formula (D),
and
wherein a difference between a pKa value of the Bronsted acid in water and a pKa value of the Bronsted base in water is 12 or more;

TABLE 24

| | Lubricating agent | Coefficient of friction after 100 times of shuttle runs | | Still durability/min | | Shuttle durability/ times | | Still durability after heating/min | | Shuttle durability after heating/times | |
|---|---|---|---|---|---|---|---|---|---|---|---|
| | | −5° C. | 40° C., 90% RH | −5° C. | 40° C., 30% RH | −5° C. | 40° C., 90% RH | −5° C. | 40° C., 30% RH | −5° C. | 40° C., 90% RH |
| Ex. 50 | Ionic liquid 12 | 0.19 | 0.23 | >60 | >60 | >200 | >200 | >60 | >60 | >200 | >200 |
| Ex. 51 | Ionic liquid 13 | 0.2 | 0.22 | >60 | >60 | >200 | >200 | >60 | >60 | >200 | >200 |
| Ex. 52 | Ionic liquid 14 | 0.21 | 0.24 | >60 | >60 | >200 | >200 | >60 | >60 | >200 | >200 |
| Ex. 53 | Ionic liquid 15 | 0.22 | 0.26 | >60 | >60 | >200 | >200 | >60 | >60 | >200 | >200 |
| Ex. 54 | Ionic liquid 16 | 0.23 | 0.26 | >60 | >60 | >200 | >200 | >60 | >60 | >200 | >200 |
| Ex. 55 | Ionic liquid 17 | 0.24 | 0.28 | >60 | >60 | >200 | >200 | >60 | >60 | >200 | >200 |
| Ex. 56 | Ionic liquid 18 | 0.23 | 0.27 | >60 | >60 | >200 | >200 | >60 | >60 | >200 | >200 |
| Comp. Ex. 31 | Comparative ionic liquid 8 | 0.45 | 0.49 | 18 | 16 | 56 | 45 | 14 | 8 | 36 | 30 |
| Comp. Ex. 32 | Comparative ionic liquid 9 | 0.5 | 0.55 | 16 | 14 | 45 | 36 | 12 | 10 | 28 | 25 |

The magnetic tape onto which the ionic liquid formed from the Bronsted acid and the Bronsted base containing a linear hydrocarbon group having 10 or more carbon atoms, and having the ΔpKa of 12 or more in water or of 6 or more in acetonitrile was applied as the lubricating agent showed excellent wear resistance, still durability, and shuttle durability. However, those having the ΔpKa of 12 or more in water or of 6 or more in acetonitrile, but containing no linear hydrocarbon group having 10 or more carbon atoms, which were presented as Comparative Examples, were greatly deteriorated in durability as with the aforementioned disks.

General Formula (1)

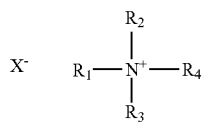

wherein at least one of $R_1$, $R_2$, $R_3$, and $R_4$ is a hydrogen atom, and at least one of $R_1$, $R_2$, $R_3$, and $R_4$ is a group which contains the linear hydrocarbon group having 10 or more carbon atoms, General Formula (2)

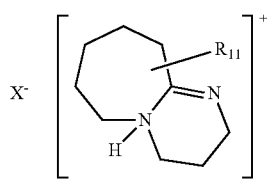

wherein $R_{11}$ denotes the linear hydrocarbon group having 10 or more carbon atoms and being attached to a carbon atom in a bicyclo ring, General Formula (3)

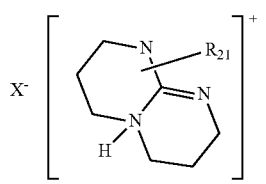

wherein $R_{21}$ denotes the linear hydrocarbon group having 10 or more carbon atoms and being attached to a carbon atom or a nitrogen atom in a bicyclo ring, Structural Formula (A)

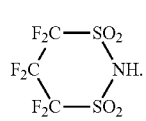

Structural Formula (B)

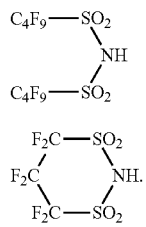

Structural Formula (C)

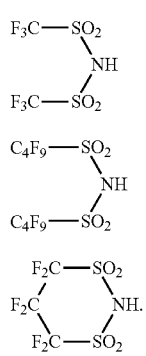

Structural Formula (D)

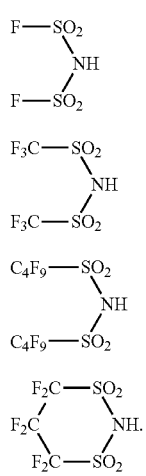

2. The magnetic recording medium according to claim 1, wherein the ionic liquid has an exothermic peak temperature determined by a differential thermal analysis (DTA) measurement of 370° C. or higher.

3. The magnetic recording medium according to claim 1, wherein the hydrocarbon group is an alkyl group.

4. A magnetic recording medium, comprising:
a non-magnetic support; and
at least a magnetic layer on or above the non-magnetic support,
wherein the magnetic layer contains a lubricating agent comprising:
an ionic liquid formed from a Bronsted acid (HX) and a Bronsted base (B),
wherein the ionic liquid is represented by the following General Formula (1), (2) or (3),
wherein the Bronsted acid is trifluoromethane sulfonic acid, a compound represented by the following Structural Formula (A), a compound represented by the following Structural Formula (B), a compound represented by the following Structural Formula (C), or a compound represented by the following Structural Formula (D),
and
wherein a difference between a pKa value of the Bronsted acid in acetonitrile and a pKa value of the Bronsted base in acetonitrile is 6 or more General Formula (1)

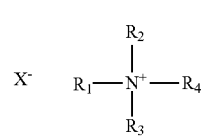

wherein at least one of $R_1$, $R_2$, $R_3$, and $R_4$ is a hydrogen atom, and at least one of $R_1$, $R_2$, $R_3$, and $R_4$ is a group which contains the linear hydrocarbon group having 10 or more carbon atoms, General Formula (2)

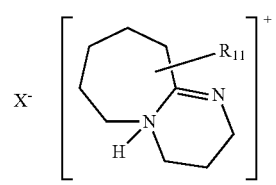

wherein $R_{11}$ denotes the linear hydrocarbon group having 10 or more carbon atoms and being attached to a carbon atom in a bicyclo ring, General Formula (3)

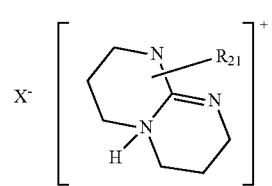

wherein $R_{21}$ denotes the linear hydrocarbon group having 10 or more carbon atoms and being attached to a carbon atom or a nitrogen atom in a bicyclo ring,

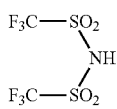
Structural Formula (A)

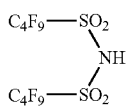
Structural Formula (B)

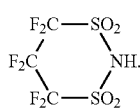
Structural Formula (C)

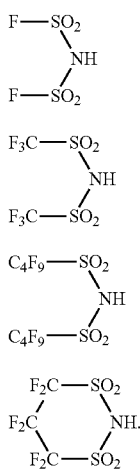
Structural Formula (D)

5. The magnetic recording medium according to claim 4, wherein the ionic liquid has an exothermic peak temperature determined by a differential thermal analysis (DTA) measurement of 370° C. or higher.

6. The magnetic recording medium according to claim 1, wherein the General Formula (2) is the following General Formula (2-1), and the General Formula (3) is the following General Formula (3-1):

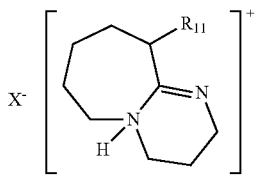
General Formula (2-1)

wherein $R_{11}$ denotes a linear hydrocarbon group having 10 or more carbon atoms,

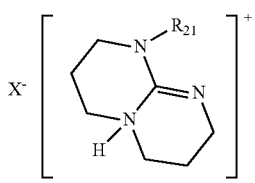
General Formula (3-1)

wherein $R_{21}$ denotes a linear hydrocarbon group having 10 or more carbon atoms.

7. The magnetic recording medium according to claim 1, wherein the number of carbon atoms in the linear hydrocarbon group is 10 or more and 25 or less.

8. The magnetic recording medium according to claim 6, wherein the number of carbon atoms in the linear hydrocarbon group is 10 or more and 25 or less.

9. The magnetic recording medium according to claim 4, wherein the General Formula (2) is the following General Formula (2-1), and the General Formula (3) is the following General Formula (3-1):

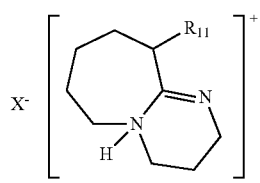
General Formula (2-1)

wherein $R_{11}$ denotes a linear hydrocarbon group having 10 or more carbon atoms,

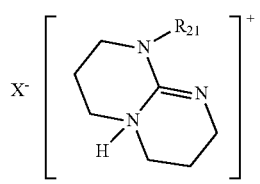
General Formula (3-1)

wherein $R_{21}$ denotes a linear hydrocarbon group having 10 or more carbon atoms.

10. The magnetic recording medium according to claim 4, wherein the number of carbon atoms in the linear hydrocarbon group is 10 or more and 25 or less.

11. The magnetic recording medium according to claim 9, where the number of carbon atoms in the linear hydrocarbon group is 10 or more and 25 or less.

\* \* \* \* \*